(12) United States Patent
Stopher

(10) Patent No.: US 6,596,107 B2
(45) Date of Patent: Jul. 22, 2003

(54) PROCESS AND APPARATUS FOR MAKING A PRE-FASTENED DIAPER

(75) Inventor: James Bennington Stopher, Pocatello, ID (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 39 days.

(21) Appl. No.: 09/793,186

(22) Filed: Feb. 26, 2001

(65) Prior Publication Data

US 2002/0119878 A1 Aug. 29, 2002

(51) Int. Cl.$^7$ ................................................. A61F 13/15
(52) U.S. Cl. ..................... 156/66; 156/200; 156/204; 156/226; 156/227; 156/271; 604/389; 604/391
(58) Field of Search ......................... 156/66, 223, 226, 156/206, 271, 202, 211, 221, 204, 269, 216, 227, 267; 604/385.04, 389, 391, 396, 385.11, 385.201

(56) References Cited

U.S. PATENT DOCUMENTS

| | | | |
|---|---|---|---|
| 4,663,220 A | | 5/1987 | Wisneski et al. |
| 5,226,992 A | | 7/1993 | Morman |
| 5,399,219 A | | 3/1995 | Roessler et al. |
| 5,531,732 A | * | 7/1996 | Wood .......................... 604/391 |
| 5,540,796 A | | 7/1996 | Fries |
| 5,595,618 A | | 1/1997 | Fries et al. |
| 5,624,429 A | | 4/1997 | Long et al. |
| 5,660,666 A | | 8/1997 | Dilnik et al. ...................... 1/1 |
| 5,716,478 A | | 2/1998 | Boothe et al. |
| 5,759,317 A | | 6/1998 | Justmann |
| 6,022,443 A | | 2/2000 | Rajala et al. |
| 6,113,717 A | * | 9/2000 | Vogt et al. .................. 156/73.1 |
| 6,149,755 A | | 11/2000 | McNichols et al. |

FOREIGN PATENT DOCUMENTS

| | | | |
|---|---|---|---|
| EP | 0 217 032 A2 | 7/1986 | |
| EP | 320989 B1 | * 4/1994 | ........... A41B/13/04 |

* cited by examiner

*Primary Examiner*—Michael W. Ball
*Assistant Examiner*—Gladys Corcoran
(74) *Attorney, Agent, or Firm*—Paul Yee; Thomas M. Parker

(57) ABSTRACT

The present invention provides a distinctive process and apparatus (20) for forming an article. The technique of the invention includes a providing of a first panel layer (22), and a positioning of a second panel layer (28) onto the first panel layer (22). An inboard portion (24) of the first panel layer (22) is attached to an inboard portion (30) of the second panel layer (28), and a side region (36) of a tab web (34) is attached to the inboard portion (24, 30) of at least one of the first and second panel layers (22, 28) to provide a first assembly web (48). A fastening mechanism (40) is attached to the tab web (34), and an outboard portion (26, 32) of at least one of the first and second panel layers (22, 28) is folded to provide a folded layer (44) and a protruding layer (46). A protruding layer portion (56) of a panel assembly (50) is attached to a first waistband portion (62) of an article segment (60), and the article segment (60) is transversely folded to provide a folded article segment. A folded layer portion (44) of the panel assembly (50) can then be attached a second waistband portion (64) of the folded article segment.

13 Claims, 23 Drawing Sheets

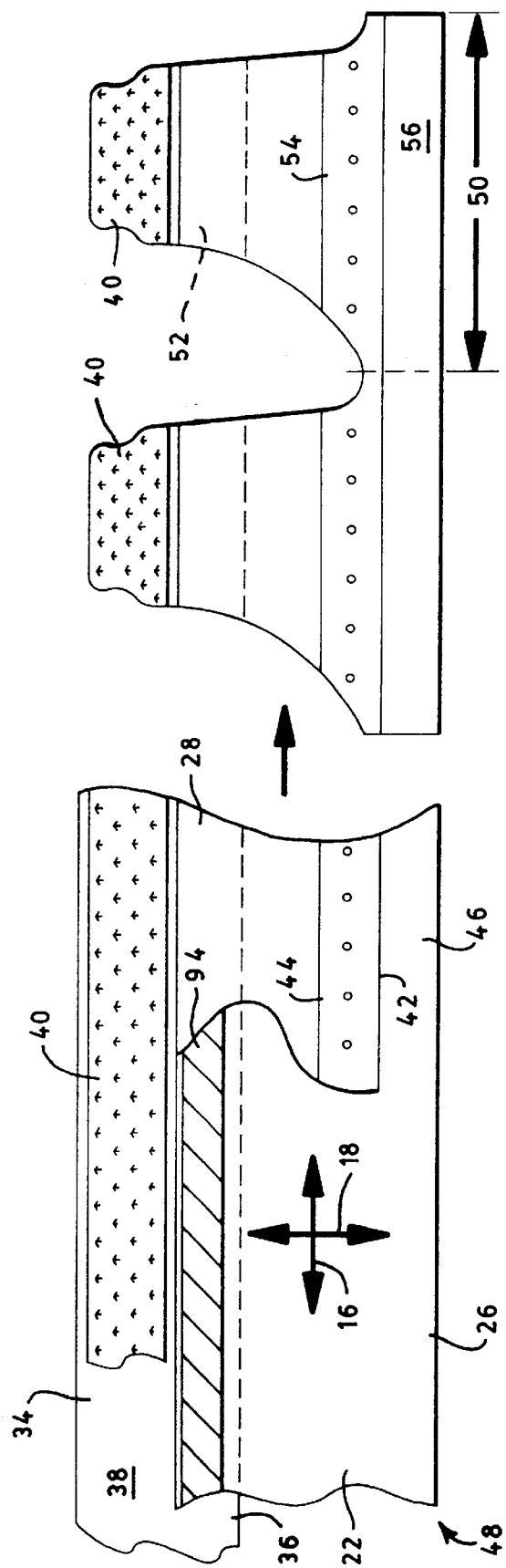

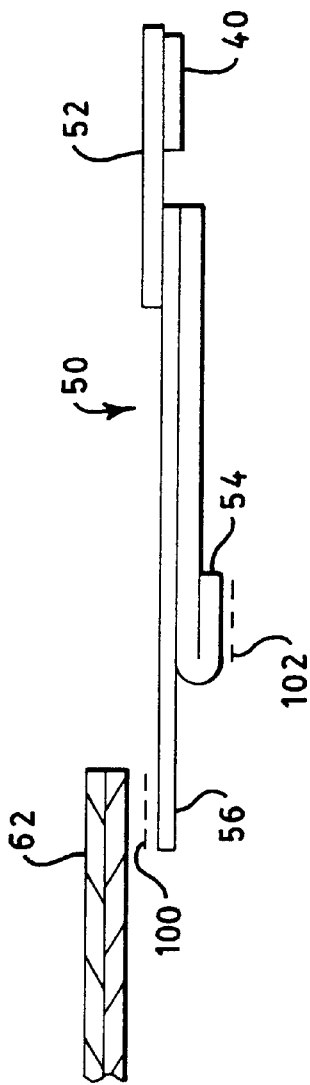
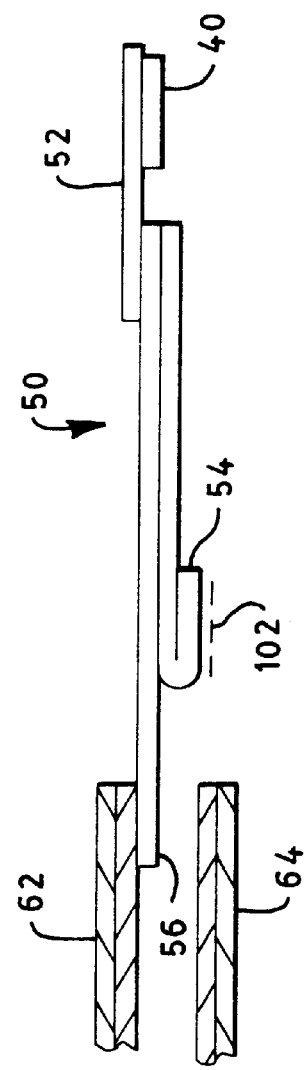

PROCESS AND APPARATUS FOR MAKING A PRE-FASTENED DIAPER

FIELD OF THE INVENTION

The present invention relates to a technique for forming an article. More particularly, the invention relates to a technique for forming an article having a prefastened, fastening system.

BACKGROUND OF THE INVENTION

Conventional absorbent articles, such as disposable diapers, have been constructed with elasticized waistbands. Particular article designs have incorporated a stretchable outer cover which can include an elastomeric web material and a layer of nonwoven fabric, and may be formed as a stretch bonded laminate. Other conventional designs have included elastomeric or nonelastomeric side panel members connected to the lateral side edges of an outercover composed of a polymer film material, and fasteners and fastening tabs have been connected and attached to the side panels for securing the article on a wearer. The fastener tabs can include adhesive fastening systems or mechanical fastening systems, such as mechanisms that include the complementary components of a hook-and-loop fastener.

Conventional techniques have been employed for forming articles which have fastening systems with generally rectangular side-panel members or with shaped side-panel members having desired edge contours. Particular techniques have been configured to remove a continuous die-cut strip from the middle region of a web of side panel material having strips of a mechanical fastener component attached thereto. Conventional processes, such as those described above, have, however, exhibited significant room for improvement when incorporated into desired, high speed manufacturing operations. For example, the process arrangements have not been sufficiently able to produce a desired pre-fastened article with an adjustable waist-size during high-speed operations. The processes also have not been sufficiently able to reliably produce an article having a pre-fastened securement system, and contoured leg openings that provide desired levels of fit and comfort. As a result, there has been a continued need for an improved manufacturing technique which can more efficiently produce an article having a reliable and easy-to-operate fastening system that is pre-fastened during manufacture.

BRIEF DESCRIPTION OF THE INVENTION

The present invention provides a distinctive process and apparatus for forming an article, such as an absorbent article. The technique of the invention can include a providing of a first panel layer having a first inboard portion and a first outboard portion. A second panel layer is positioned onto the first panel layer, and the second panel layer includes a second inboard portion and a second outboard portion. The inboard portion of the first panel layer can be attached to the inboard portion of the second panel layer, and a side region of a tab web can be attached to the inboard portion of at least one of the first and second panel layers to provide a first assembly web. A fastening mechanism can be provided in an arrangement attached to an appointed securement surface of the tab web, and the outboard portion of at least one of the first and second panel layers can be folded to thereby provide a folded layer and a protruding layer. Additionally, the first assembly web can be severed to provide a plurality of individual panel assemblies, and each panel assembly can be configured to include a tab web portion, a folded layer portion, and a protruding layer portion. An article segment can be provided with the article segment having a first waistband portion, a second waistband portion, and an intermediate portion that interconnects the first and second waistband portions. The protruding layer portion of at least one panel assembly can be attached to a side section of the first waistband portion of the article segment, and the article segment can be folded along a transversely extending fold line to provide a folded article segment. Additionally, the folded layer portion of at least one panel assembly can be attached to a side section of the second waistband portion of the folded article segment.

In a particular aspect, the severing of the first assembly web can include a severing of the first panel layer, the second panel layer and the tab web. In another aspect, the disclosed process and apparatus can further include a turning of the folded layer portion of at least one panel assembly around the side section of the second waistband portion of the folded article segment. Additionally, the technique of the invention can include a turning of the tab web portion of at least one panel assembly around the side section of the second waistband portion of the folded article segment.

The various aspects of the invention can advantageously provide an improved technique for manufacturing a fully assembled, three-dimensional article, such as a pre-fastened diaper. The invention can incorporate a distinctive side panel member, and the side panel member can be configured to provide an adjustment feature. In a particular aspect, the side panel member can provide a "Y-ear" component, and in another aspect, the invention can employ a distinctive folding process to more efficiently produce the desired, prefastened article. With the technique, the prefastened article can be manufactured at high speed, and the resultant article can be more effectively and efficiently produced without complicated mechanisms for holding, folding and/or stretching the side panel members. As a result, the present invention, in its various configurations, can provide an improved technique for more reliably forming an article having a more versatile fastening system. Additionally, the invention can more effectively avoid alignment problems that have been associated with prior manufacturing systems. The resultant article and fastening system can have more consistent quality and can provide more dependable performance.

BRIEF DESCRIPTION OF THE DRAWINGS

The invention will be more fully understood and further advantages will become apparent when reference is made to the following detailed description and accompanying drawings in which:

FIG. 5 representatively shows a top view of a sequence wherein the assembly web (in a partially cut-away view) has been folded along a longitudinally extending fold line before a subsequent shaping of the assembly web;

FIG. 14 representatively shows a schematic, expanded, edgewise view of a panel assembly which is operatively joined and attached to a first waistband portion of an article segment;

FIG. 14A representatively shows a schematic, expanded, edgewise view of a panel assembly which is assembled to a first waistband portion of an article segment, wherein the article segment has been folded and the first and second waistband portions of the article segment have been brought into an operative proximity to each other;

DETAILED DESCRIPTION OF THE INVENTION

The method and apparatus of the present invention will be described herein in relationship to their use in producing a fastener system for absorbent articles, particularly disposable absorbent articles. Such articles can be placed against or in proximity to the body of a wearer to absorb and contain various exudates discharged from the body, and are intended to be discarded after a limited period of use. The articles are not intended to be laundered or otherwise restored for re-use. While the present description will particularly be made in the context of a diaper article, it should be understood that the present invention is also applicable to other articles, such as caps, gowns, drapes, covers, adult incontinence garments, sanitary napkins, children's training pants, and the like.

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The present disclosure will be expressed in terms of its various components, elements, constructions, configurations, arrangements and other features that may also be individually or collectively be referenced by the term, "aspect(s)" of the invention, or other similar terms. It is contemplated that the various forms of the disclosed invention may incorporate one or more of its various features and aspects, and that such features and aspects may be employed in any desired, operative combination thereof.

Figure 15:
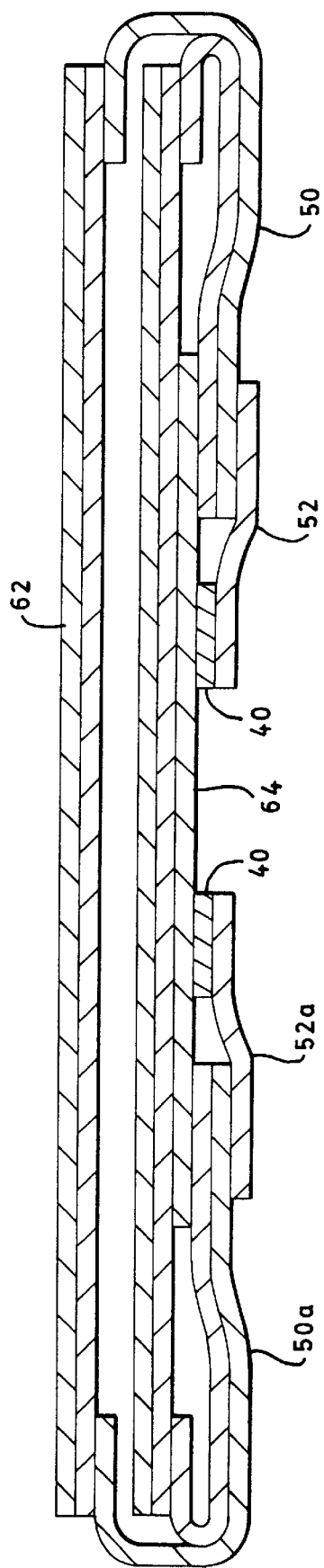
FIG. 15 shows a schematic, edgewise, end view of a representative folded article having a pair of fastener/panel assemblies attached to the side margins of the first and second waistband portions of the article.
Figure 16:
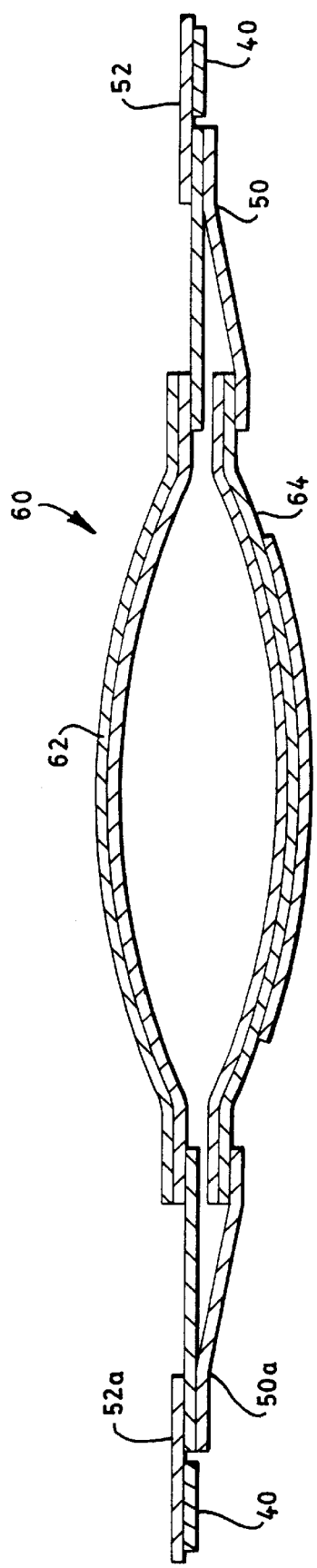
FIG. 16 shows a schematic, edgewise, end view of a representative folded article wherein the fastener/panel assemblies have been unfastened and moved to open positions.
Figure 17:
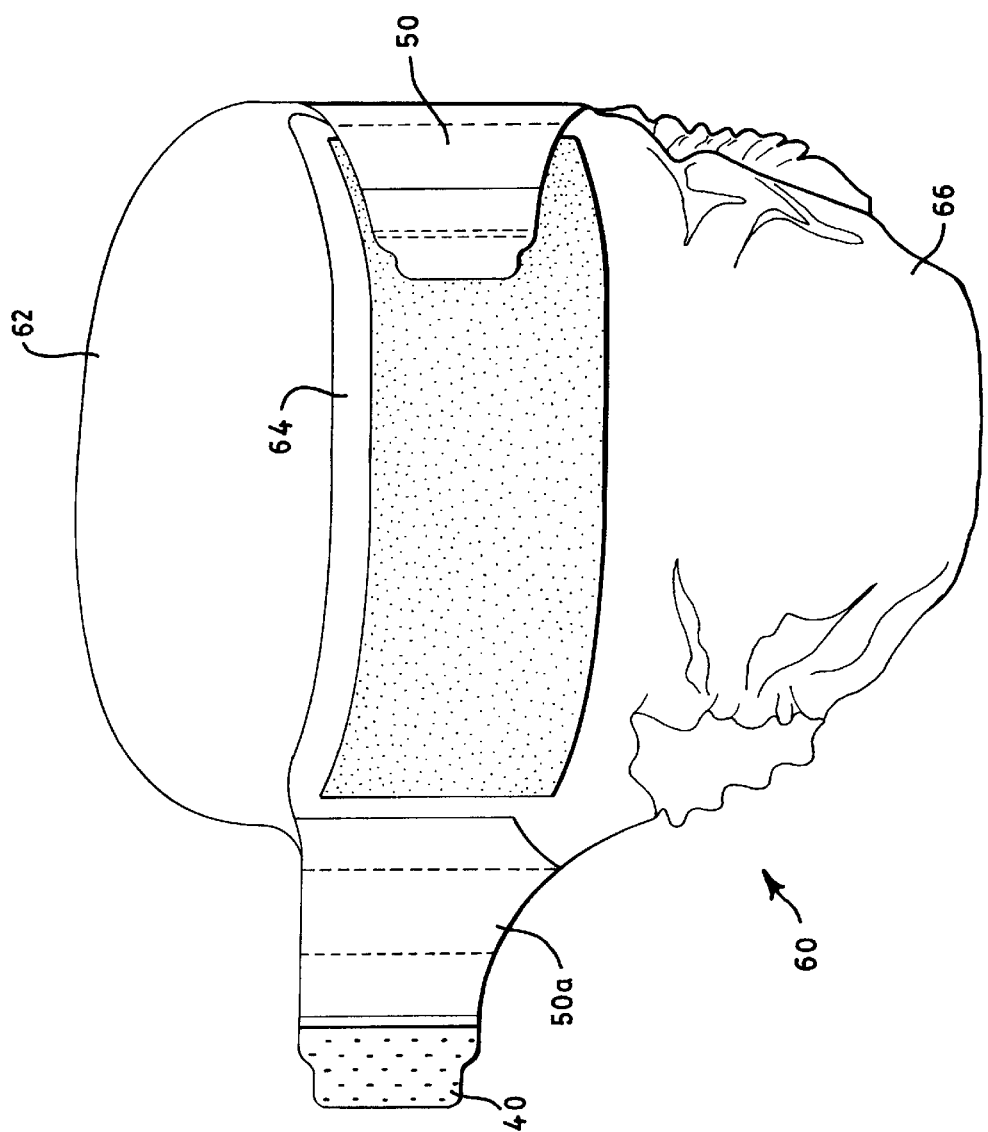
FIG. 17 shows a schematic, perspective view of a representative pre-fastened article that can be produced with the present invention.

With reference to FIGS. 15, 16 and 17, the present invention can advantageously be employed to more efficiently produce a fastening system for incorporation into an absorbent article, such as the representatively shown disposable diaper having a front waistband section, a rear waistband section, and an intermediate section which interconnects the front and rear waistband sections. The article can include a backsheet layer, and a liquid permeable topsheet layer which is superposed on and connected to the backsheet layer. Desirably, the backsheet layer is configured to be substantially liquid-impermeable. An absorbent body is located between the backsheet layer and the topsheet layer, and a fastening system can be connected to the article at either or both of the laterally opposed end regions of at least one of the front and rear waistband sections. The fastening or securement system can include an adhesive fastening mechanism, a mechanical fastening mechanism or the like, as well as combinations thereof. Each fastening system can include an assembly having one or more side panel members, and one or more of the side panel members can optionally be constructed to be elastomerically stretchable along at least a lateral, cross-direction of the article. In a pre-fastened article, the side panel members and their corresponding fastening systems can be assembled during manufacture to operatively pre-attach and pre-connect the front and rear waistband sections of the article to thereby encircle a wearer's body during the intended use. The fastening systems can provide a fastening tab portion operatively joined to its associated, corresponding side panel assembly for securing the article on the wearer. In desired arrangements, the fastening tab portions can be selectively released and repositioned to adjust the fit of the article to match the individual wearer. In particular aspects, the method and apparatus of the invention can be configured to apply and attach a diaper ear to provide a pre-fastened diaper Articles which include elastomeric side panels and selectively configured fastener tabs are described in U.S. patent application Ser. No. 168,615 to T. Roessier el al, entitled DYNAMIC FITTING DIAPER, and filed Dec. 16, 1993 (attorney docket No. 10,961), now abandoned; and in U.S. Pat. No. 5,624,429 entitled MECHANICAL FASTENING SYSTEM WITH GRIP TAB, by A. Long et al. which was issued Apr. 29, 1997 (attorney docket No. 12,563). Various techniques forming the fastening systems are described in U.S. Pat. No. 5,399,219 entitled METHOD FOR MAKING A FASTENING SYSTEM FOR A DYNAMIC FITTING DIAPER by T. Roessier et al. which was issued Mar. 21, 1995 (attorney docket No. 11,186); in U.S. Pat. No. 5,540,796, entitled A PROCESS FOR ASSEMBLING ELASTICIZED EAR PORTIONS by D. Fries which was issued Jul. 30, 1996 (attorney docked No. 11,169); and in U.S. Pat. No. 5,595,618 entitled AN ASSEMBLY PROCESS FOR A LAMINATED TAPE by D. Fries et al. which was issued Jan. 21, 1997 (attorney docket No. 11,950). The entire disclosures of the above-mentioned documents are incorporated herein by reference in a manner that is consistent (not in conflict) herewith.

Figure 1:
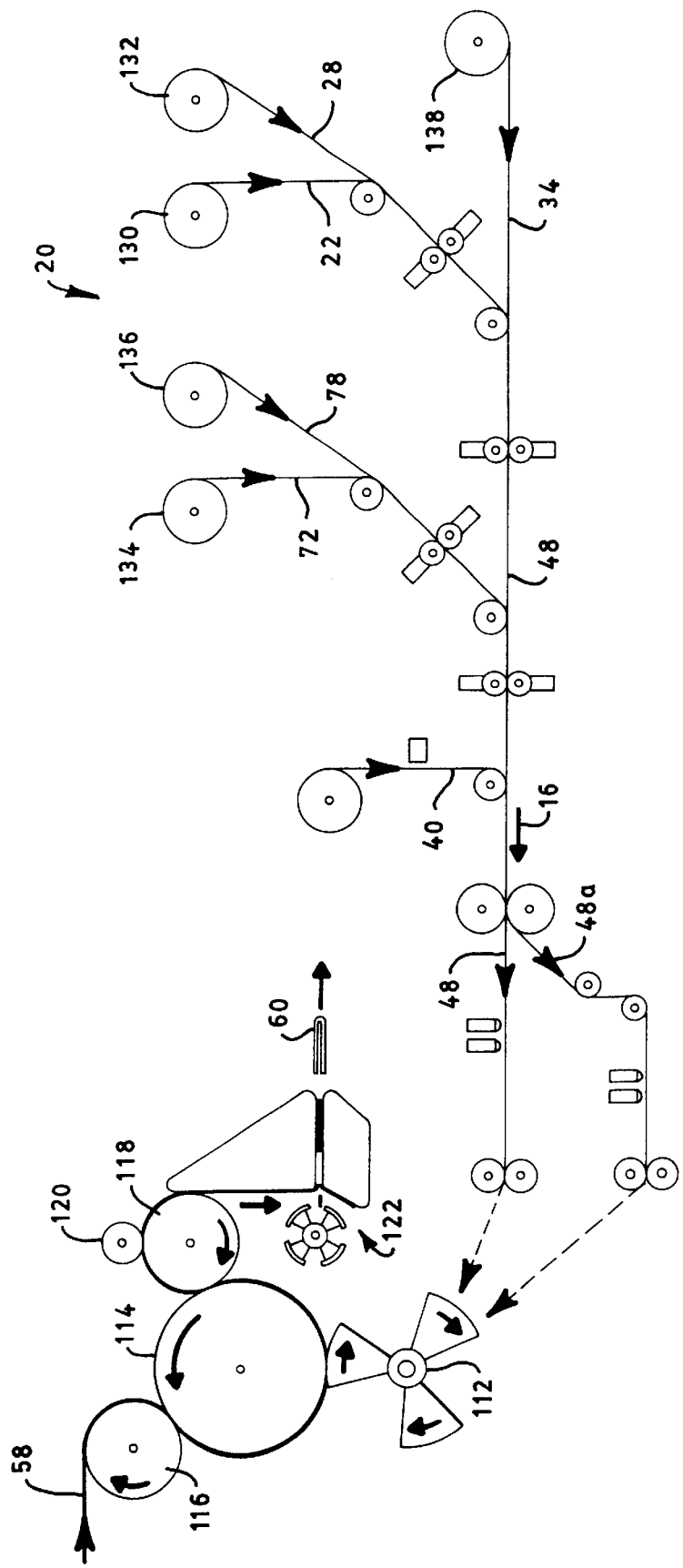
FIG. 1 representatively shows a schematic view of the method and apparatus of the invention.
Figure 9:
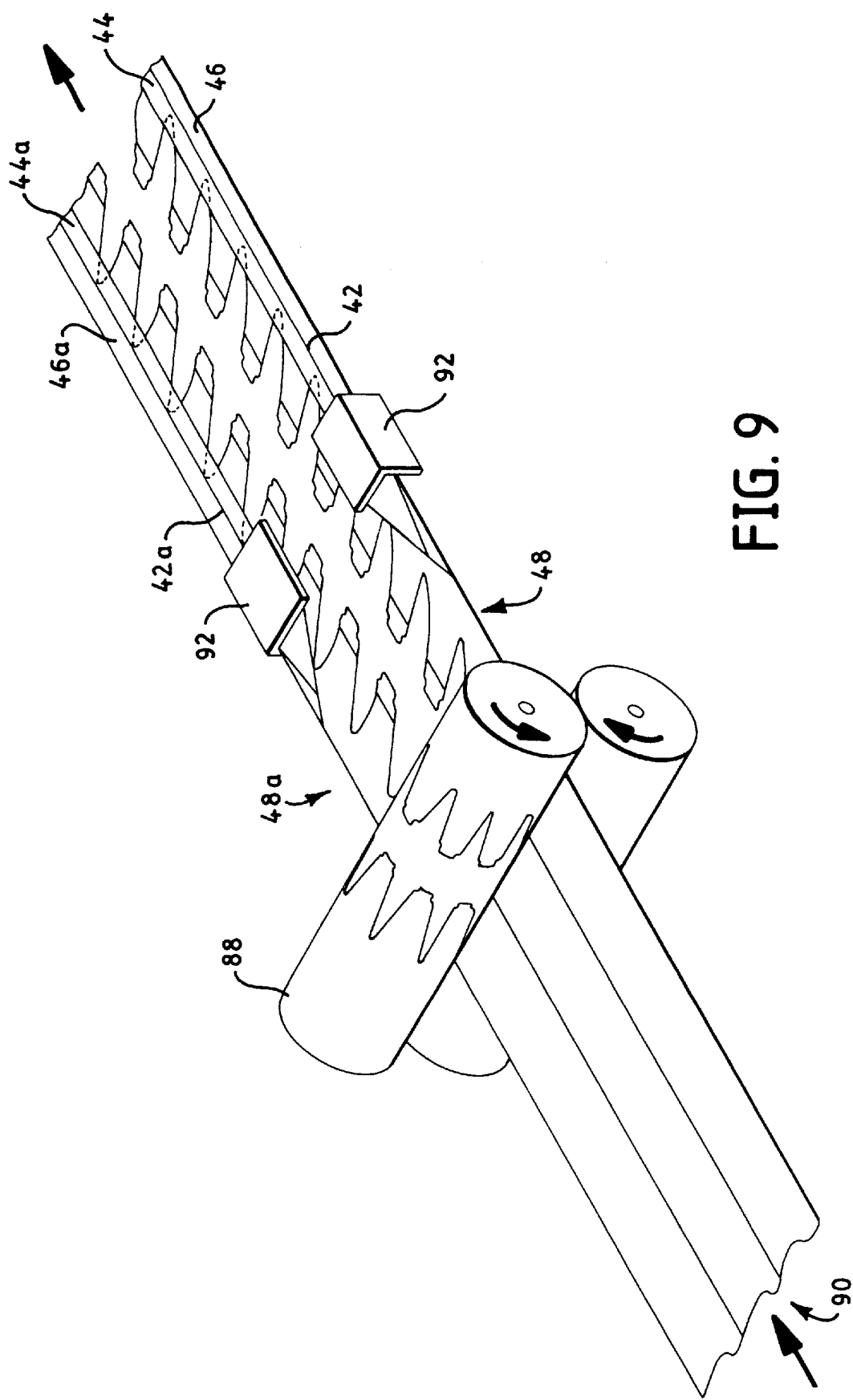
FIG. 9 shows a schematic, perspective view of a representative system for folding each individual assembly web after the dividing and shaping of the composite web to provide a set of the assembly webs.
Figure 10:
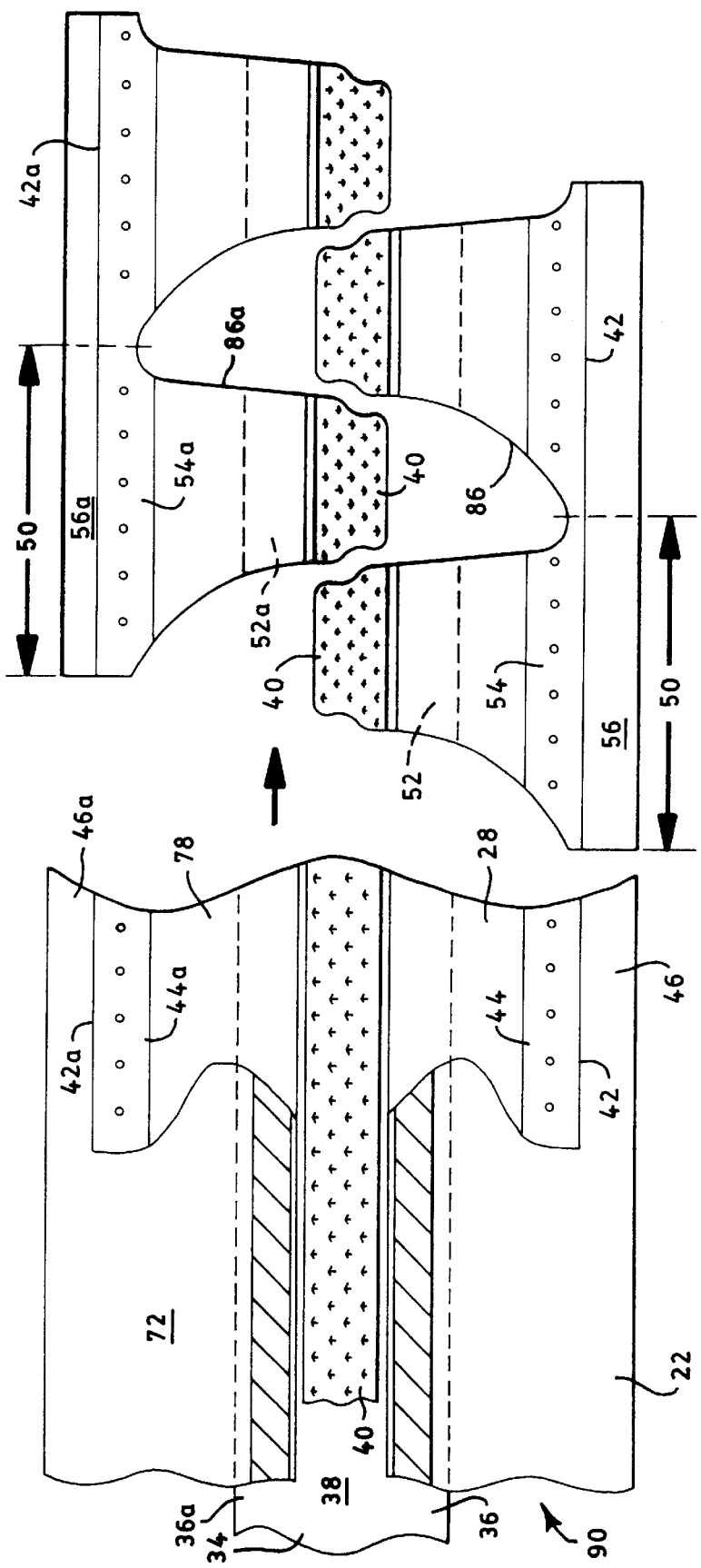
FIG. 10 representatively shows a schematic, top view of a sequence wherein the composite web (in a partially cut-away view) has been folded along longitudinally extending fold lined before a subsequent dividing and shaping of the composite web to provide a set of assembly webs.
Figure 12:
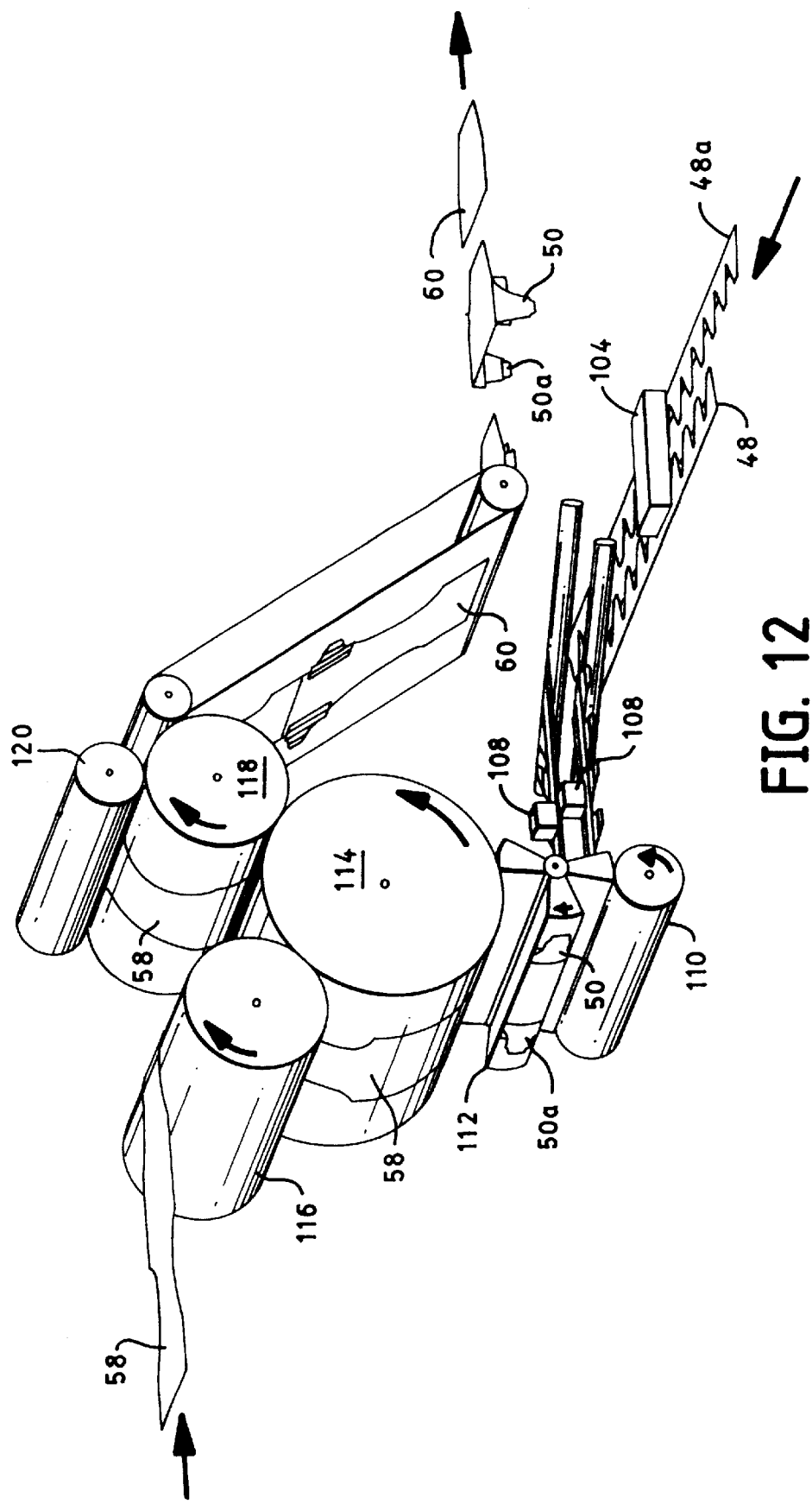
FIG. 12 shows a schematic, perspective view of a representative system for forming individual fastener/panel assemblies, and applying and assembling the individual panel assemblies to an article web to provide a series of final articles.

With reference to FIGS. 1, 9 and 12, the present invention can provide a distinctive process and apparatus 20 for forming a selected article 60, such as an absorbent article. The absorbent article can, for example, be a disposable diaper, as representatively shown. In its various process and apparatus aspects, the technique of the invention includes a providing of a first panel layer 22 having a first inboard portion 24 and a first outboard portion 26. A second panel layer 28 can be positioned onto the first panel layer 22, and the second panel layer 28 can include a second inboard portion 30 and a second outboard portion 32. The inboard portion 24 of the first panel layer 22 can be operatively attached or otherwise joined to the inboard portion 30 of the second panel layer 28, and a side region 36 of a tab web 34 can be operatively attached or otherwise joined to the inboard portion 24, 30 of at least one of the first and second panel layers 22, 28 to provide a first assembly web 48. A fastening mechanism 40 can be provided in an arrangement which can be operatively attached or otherwise joined to an appointed securement surface 38 of the tab web 34. Additionally, the outboard portion 26, 32 of at least one of the first and second panel layers 22, 28 can be folded to thereby provide a folded layer 44 and a protruding layer 46. For example, the at least one panel layer can be folded along a longitudinally extending fold line 42. The first assembly web 48 can be severed to provide a plurality of individually panel assemblies 50. Each panel assembly 50 can be configured to include a tab web portion 52, a folded layer portion 54, and a protruding layer portion 56. An article segment 60 can be provided with the article segment having a first waistband portion 62, a second waistband portion 64, and an intermediate portion 66 that interconnects the first and second waistband portions. The protruding layer portion 56 of at least one panel assembly 50 can be attached to a side section 68 of the first waistband portion 62 of the article segment 60, and the article segment 60 can be transversefolded along a transversely extending fold line to provide a folded article segment. The folded layer portion 44 of the at least one panel assembly 50 can be attached to a side section 70 of the second waistband portion 64 of the folded article segment.

In a particular aspect, the severing of the first assembly web 48 can include a severing of the first panel layer 22, the second panel layer 28 and the tab web 34. In another aspect, the process and apparatus can further include a turning of the folded layer portion 54 of the at least one panel assembly 50 around the side section 70 of the second waistband portion 64 of the folded article segment. Additionally, the technique of the invention can further include a turning of the tab web portion 52 of the at least one panel assembly 50 around the side section 70 of the second waistband portion 64 of the folded article segment.

Still another aspect can include a providing of a third panel layer 72 having a third inboard portion 74 and a third outboard portion 76. A fourth panel layer 78 can be positioned onto the third panel layer 72, and the fourth panel layer 78 can have a fourth inboard portion 80 and a fourth outboard portion 82. The inboard portion 74 of the third panel layer 72 can be attached to the inboard portion 80 of the fourth panel layer 78. Additionally, a second side region 36a of the tab web 34 can be attached to the inboard portion of at least one of the third and fourth panel layers 72, 78. A further aspect can include a dividing of at least the tab web 34 along at least one generally longitudinally extending serpentine line 86 to provide the first assembly web 48 and at least a second assembly web 48a.

Figure 2:
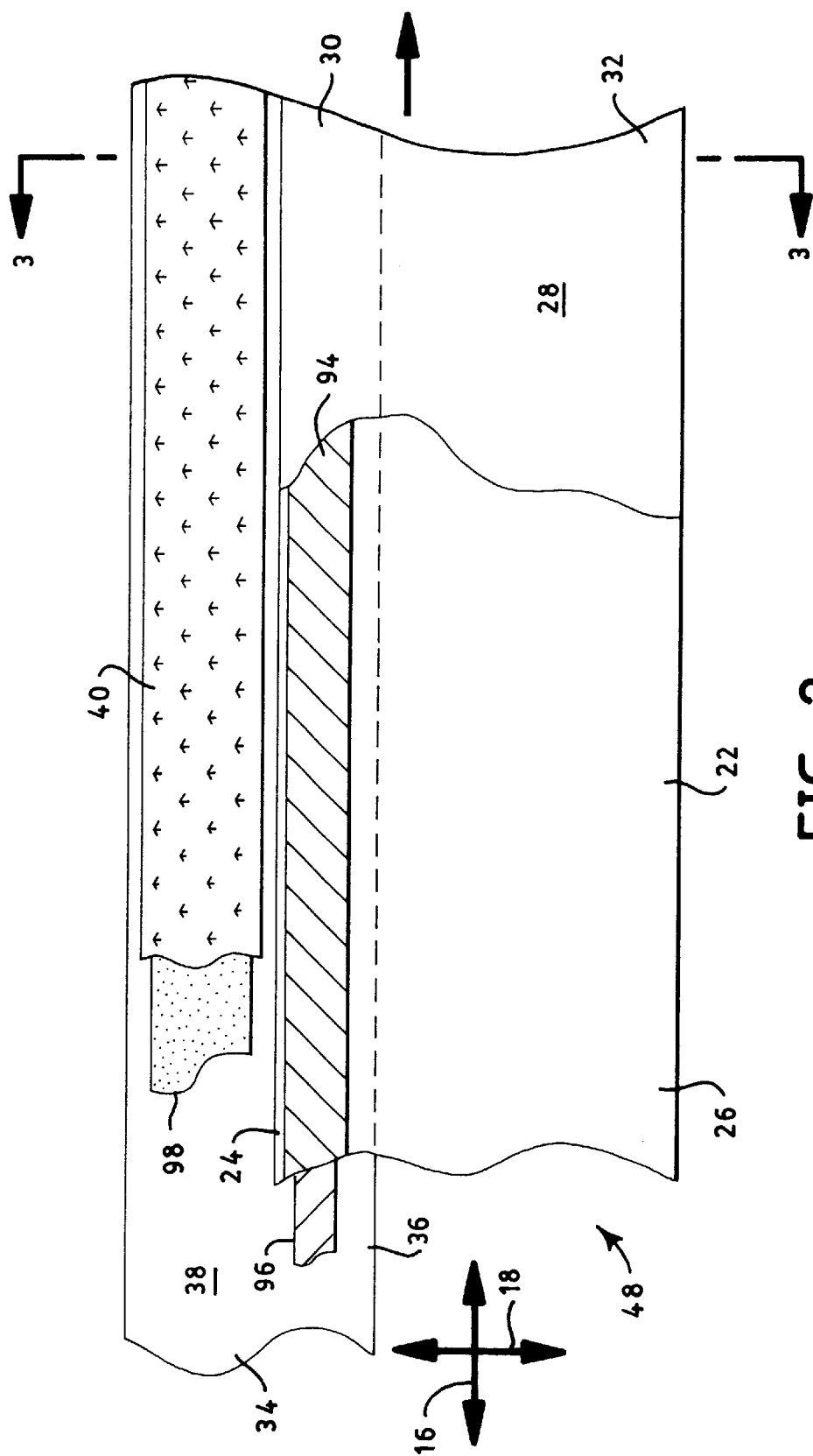
FIG. 2 representatively shows a partially cut-away, top view of a portion of a web assembly that can be produced by the method and apparatus of the invention.

As representatively shown in FIGS. 1 and 2, the method and apparatus can generally have a longitudinal, machine-direction 16 and a lateral or transverse, cross-direction 18. At any particular, selected location along the method and apparatus, the machine-direction is the generally lengthwise direction along which a particular web (or composite web) of material is moving or transported through the process. The cross-direction extends generally along the plane of the web of material, and is perpendicular to the particular machine-direction established by the method or apparatus at the selected location.

The first panel layer 22 can be delivered from a first panel layer supply 130, the second panel layer 28 can be delivered from a second panel layer supply 132, and the tab web 34 can be delivered from a suitable tab web supply 138. In desired arrangements, the third panel layer 72 can be delivered from a suitable third panel layer supply 134, and the fourth panel layer 78 can be delivered from a suitable fourth panel layer supply 136.

In particular configurations, at least one, or both, of the first and second panel layers 22, 28 can include an elastomeric material that is elastomerically stretchable. The material may include a woven fabric, knitted fabric, nonwoven fabric, polymer film or the like, as well as combinations thereof. The elastomeric material may, for example, include a styrene block polymer such as a KRATON elastomer (available from Shell Oil Company), a metallocene catalyzed elastomer, a polyurethane elastomer, a polyether amide elastomer, a polyester elastomer, or the like, as well as combinations thereof. Similarly, either or both the third and fourth panel layers 72, 78 can include an elastomeric material. Additionally, the tab web 34 can include an elastomeric material. In particular configurations, the elastomeric material can be arranged to be elastomerically stretchable at least along the cross-direction 18. The elastomeric material can, for example, be a stretch-bonded-laminate (SBL) material, a neck-bonded-laminate (NBL) material, an elastomeric film, an elastomeric foam material or the like, as well as combinations thereof. For example, suitable meltblown elastomeric fibrous webs for forming panel web 56 are described in U.S. Pat. No. 4,663,220 issued May 5, 1987 to T. Wisneski et al., the entire disclosure of which is hereby incorporated by reference. Examples of composite fabrics comprising at least one layer of nonwoven textile fabric secured to a fibrous elastic layer are described in European Patent Application EP 0 217 032 A2 which was published on Apr. 8, 1987 with the inventors listed as J. Taylor et al., the entire disclosure of which is hereby incorporated by reference. Examples of NBL materials are described in U.S. Pat. No. 5,226,992 issued Jul. 13, 1993 to M. Mormon, the entire disclosure of which is hereby incorporated by reference. A particular neck-bonded-laminate (NBL) can include a film of elastomer material sandwiched between two layers of spunbond material. The film can include a KRATON elastomer (available from Shell Oil Company), and the spunbond layers can include spunbond, polypropylene fibers.

In other arrangements, one or more of the first panel layer, second panel layer, third panel layer, fourth panel layer and tab web can be a substantially non-elastomeric. These components can include a substantially non-elastomeric material, and the material may include a woven fabric, knitted fabric, nonwoven fabric, polymer film or the like, as well as combinations thereof. The fabrics may include natural fibers or synthetic polymer fibers. The polymers employed in the non-elastomeric material may, for example, include polypropylene, polyethylene, polyester, nylon, or the like, as well as combinations thereof.

During the operation of the process and apparatus, the attaching of the various components can employ any conventional securement mechanism. Such securement mechanisms are well known in the art and can, for example, include pressure bonding, laser bonding, microwave bonding, adhesive bonding, cohesive bonding, thermal bonding, sonic bonding, sewing, rivets, staples, "hook"-and-"loop" attachments, another interengaging mechanical attachment, or the like, as well combinations thereof. The representatively shown configurations can desirably employ adhesive bonding techniques. Such adhesive bonding techniques can, for example, include hot melt adhesives, pressure sensitive adhesives, or the like, as well as combinations thereof.

The second panel layer 28 is positioned onto the first panel layer 22 by employing any suitable, conventional transport system, such as the representatively shown system of guide rollers. Desirably, the inboard portion 24 of the first panel layer 22 is substantially, permanently attached to the inboard portion 30 of the second panel layer 28 employing a suitable attaching mechanism 94. In the representatively shown arrangement, for example, a sonic bonding system can be employed to form the desired attachment and securement. The attached inboard portions of the first and second panel layers may or may not have inboard edges that are arranged to be coterminous.

The side region 36 of the tab web 34 is attached to the inboard portion 24, 30 of at least one of the first and second panel layers 22, 28 with an operative securement 96 to provide a first assembly web 48. As representatively shown, the tab web can be configured to extend beyond the corresponding terminal edges of the first and second panel layers. The tab web 34 can be attached to the at least one panel layer before or after the first and second panel layers have been attached to each other, as desired.

The securement of the inboard portion 24 of the first panel layer 22 to the inboard portion 30 of the second panel layer 28 and the securement of the tab web 34 to the inboard portion 24, 30 of at least one of the first and second panel layers 22, 28 may be conducted in a single, substantially simultaneous attaching operation, or in separate attaching operations. For example, where the first and second panel layers are substantially coterminous, the securement of the inboard portion 24 of the first panel layer 22 to the inboard portion 30 of the second panel layer 28 and the securement of the tab web 34 to the inboard portion 24, 30 of at least one of the first and second panel layers 22, 28 may conveniently be conducted in a single attaching operation. Where the first and second panel layers are not coterminous, there can be a significant offset distance between the terminal edge of the first panel layer and the associated terminal edge of the second panel layer. Accordingly, the securement of the first and second layers to each other and the securement of the tab web may conveniently be conducted in separate attaching operations.

The fastening mechanism 40 is provided in an arrangement which is operatively attached or otherwise joined to an appointed securement surface 38 of the tab web 34 with an operative attachment 98. The fastening mechanism may have been secured to the tab web prior to introducing the tab web into the present process. Alternatively, the fastening mechanism may be assembled and secured to the tab web during the operation of the presently disclosed process. In the shown arrangement, the fastening mechanism 40 is provided in the form of a single strip of fastening material. The fastening mechanism may alternatively be in the form of multiple strips, or any other operative configuration.

Any suitable fastening mechanism may be employed. Such fastening mechanisms can include adhesive fasteners, cohesive fasteners, interengaging mechanical fasteners or the like, as well as combinations thereof. For example, the fastening mechanism can include a cooperating component of a conventional "hook-and-loop" fastener, the structures of which are well known in the art. In the representatively shown arrangement the selected fastening mechanism is a "hook" material. Such hook materials may have hook elements in various shapes, configurations and distribution patterns. For example, the hook elements may have the general shape of an inverted "J", a "T", a mushroom, a nail head or the like, as well as combinations thereof. Optionally, the selected fastening mechanism 40 may include a conventional "loop" material. Such loop materials may include knitted fabrics, woven fabrics, nonwoven fabrics or the like, as well as combinations thereof.

Figure 3:
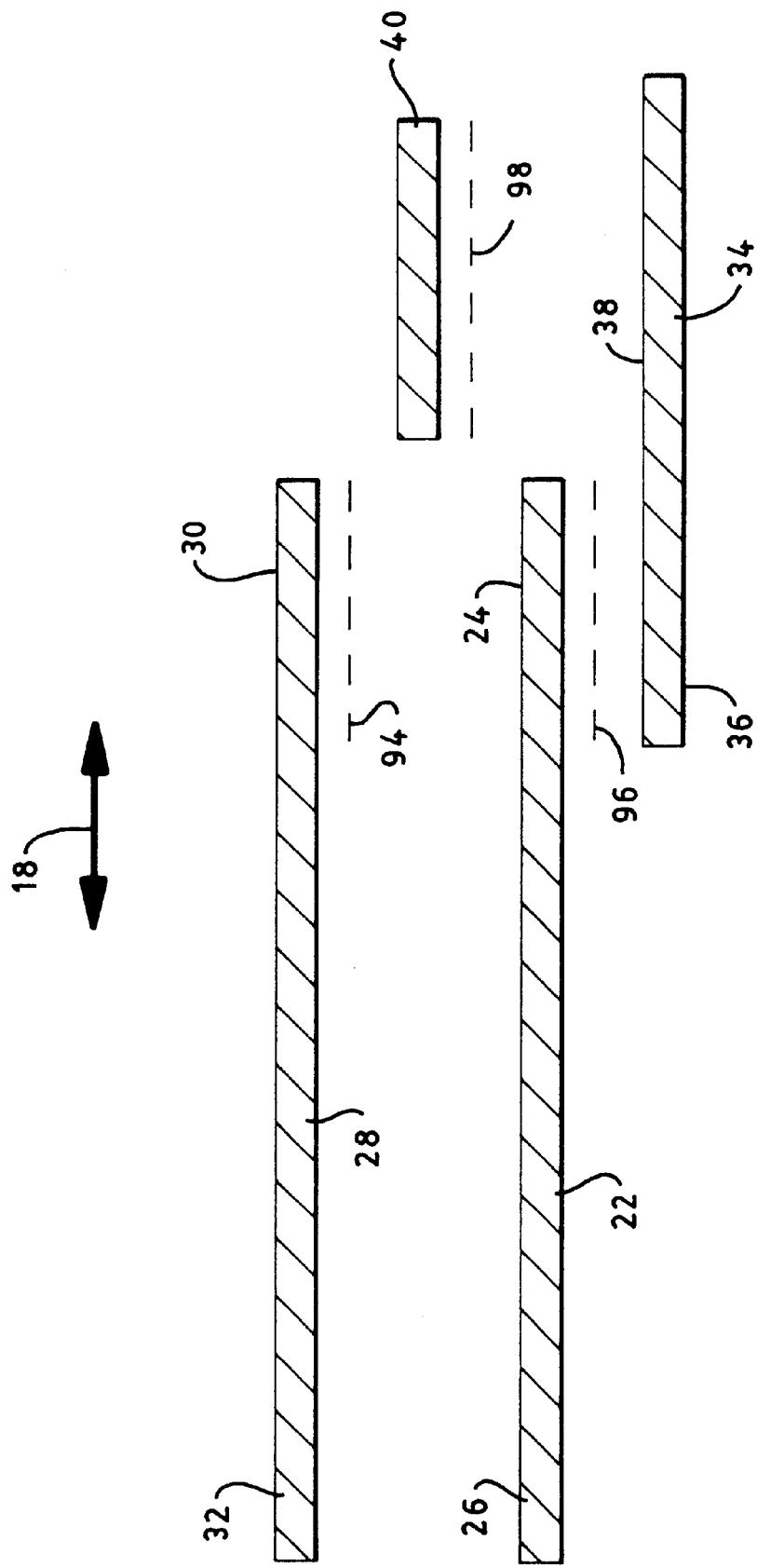
FIG. 3 representatively shows a schematic, expanded, cross-sectional end view taken along line 3—3 of FIG. 2.
Figure 3A:
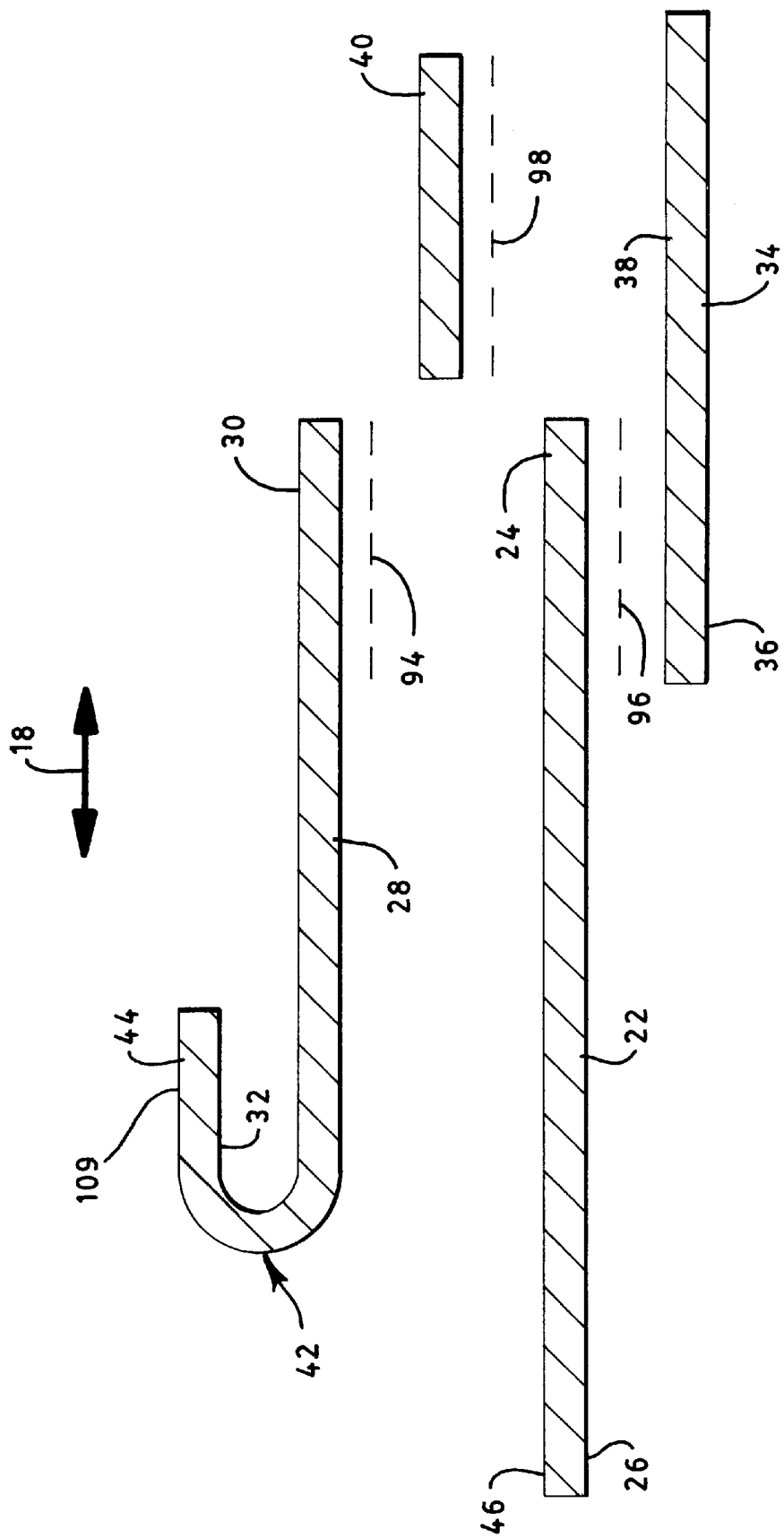
FIG. 3A representatively shows a schematic, expanded, cross-sectional end view of the web assembly illustrated in FIG. 3 after a portion of a panel layer has been folded.
Figure 4:
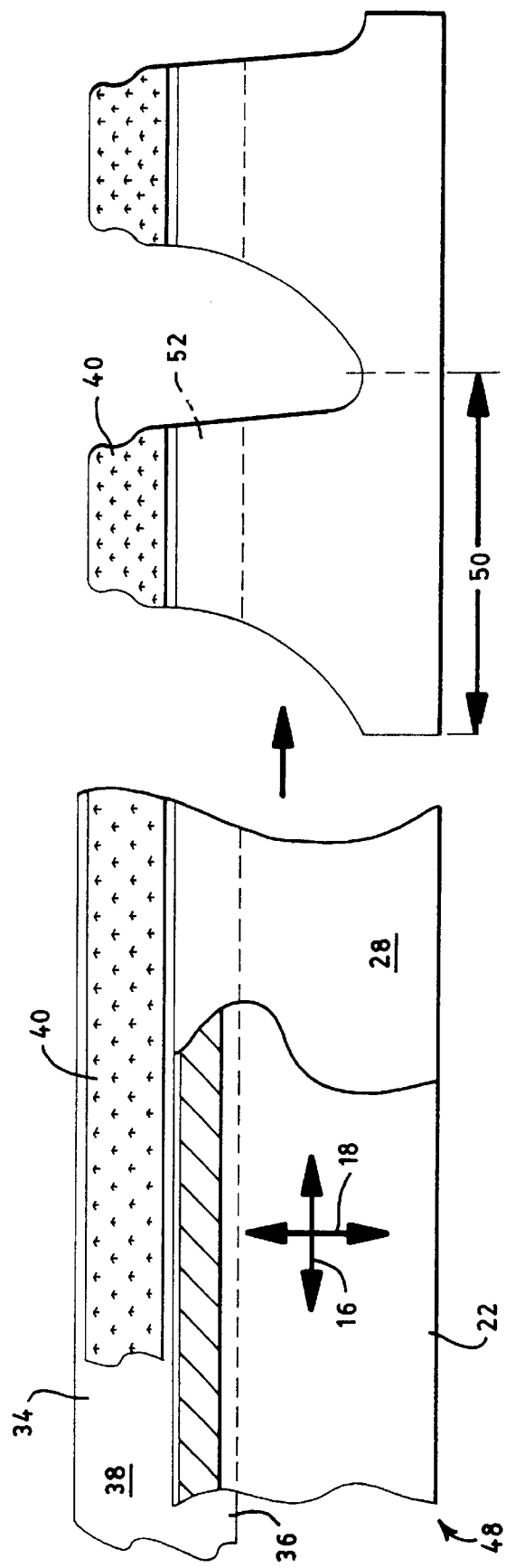
FIG. 4 representatively shows a schematic top view of a sequence wherein an assembly web (in a partially cut-away view) has been processed and shaped to provide an interconnected series of individual panel assemblies.
Figure 4A:
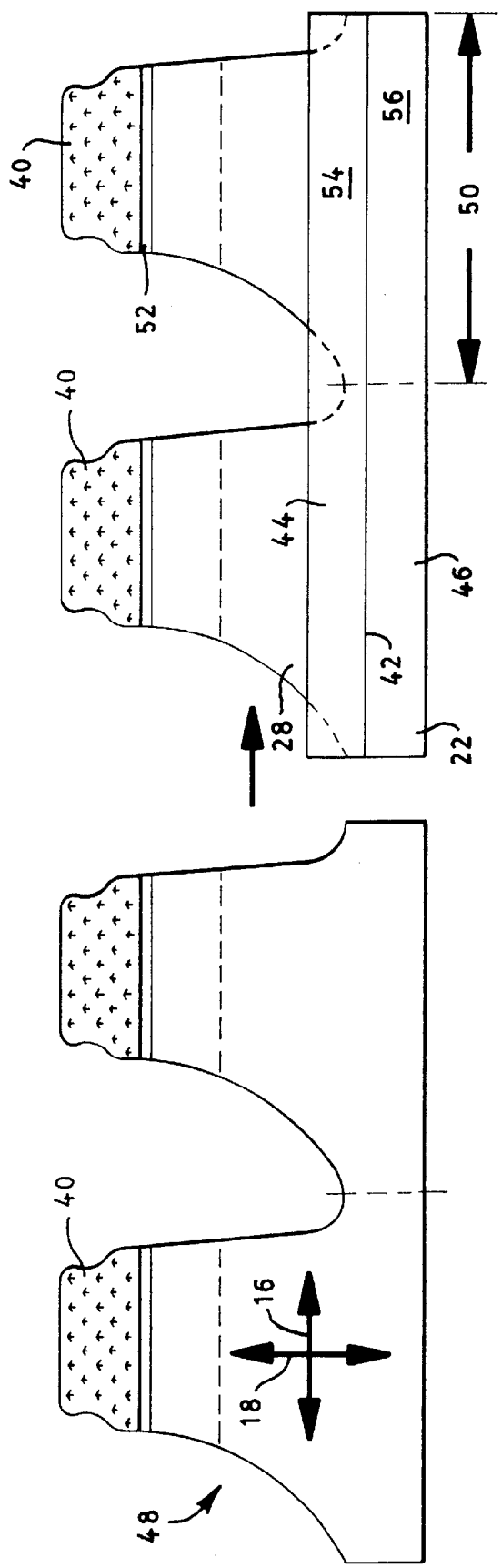
FIG. 4A representatively shows a schematic, top view of a sequence wherein a shaped assembly web (in a partially cut-away view) has been folded along a longitudinally extending fold line after the shaping of the assembly web.
Figure 6:
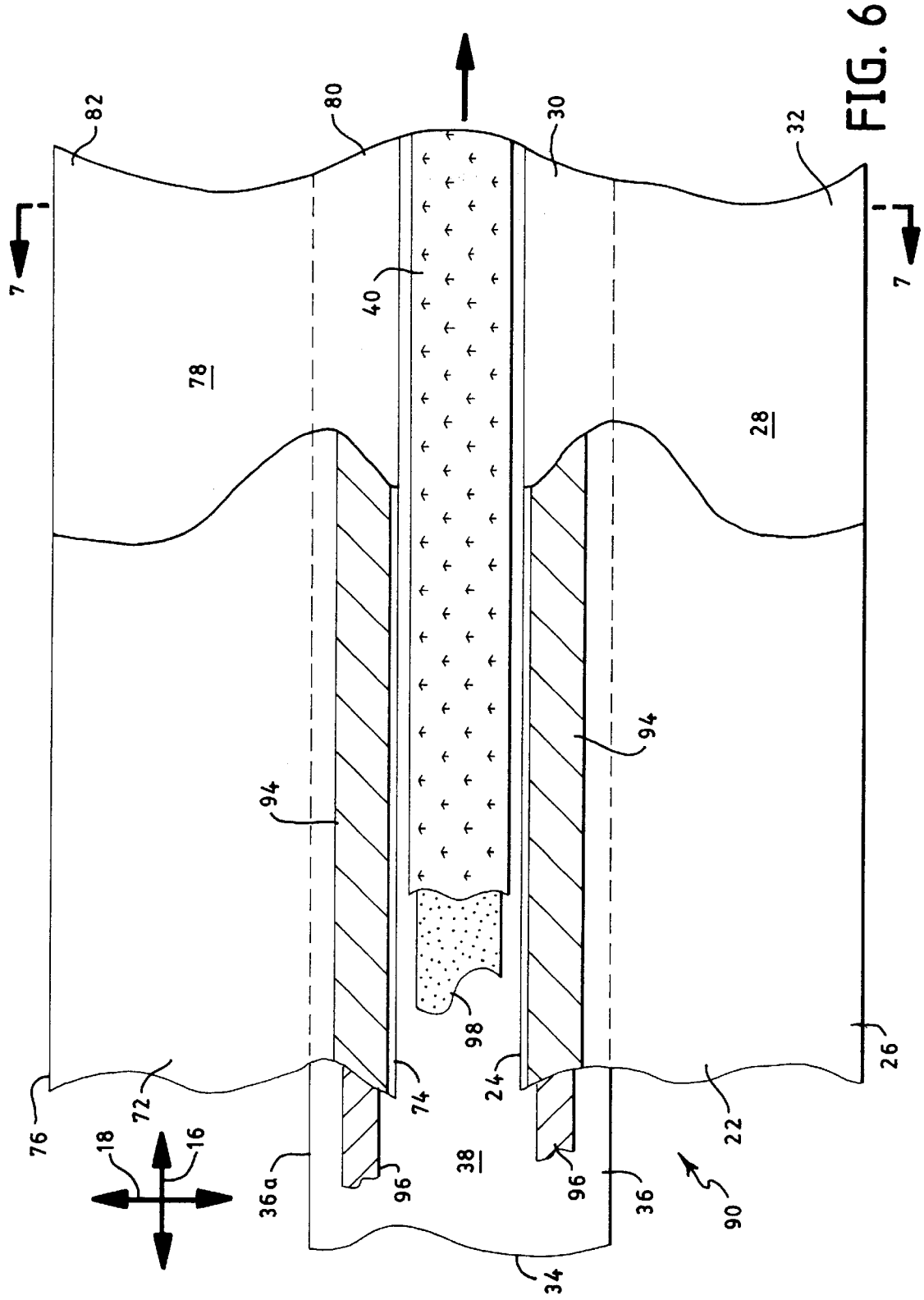
FIG. 6 representatively shows a partially cut-away, top view of a portion of a composite web that can be produced by the method and apparatus of the invention.
Figure 7:
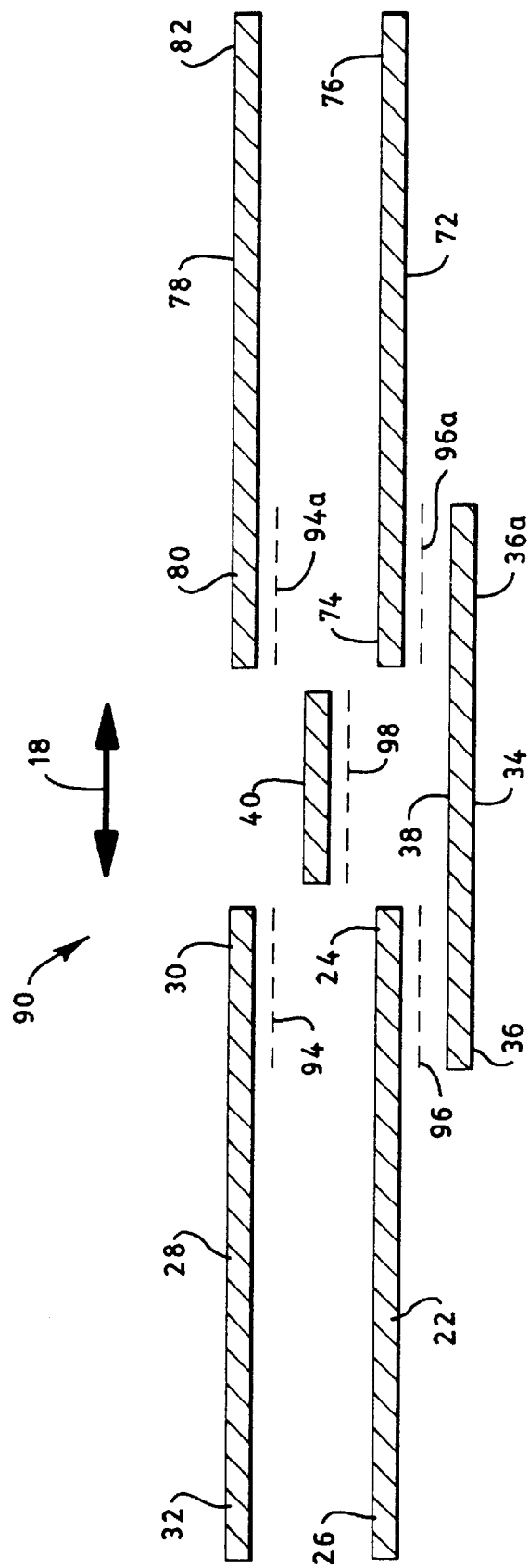
FIG. 7 representatively shows a schematic, expanded, cross-sectional, end view taken along line 7—7 of FIG. 6.
Figure 7A:
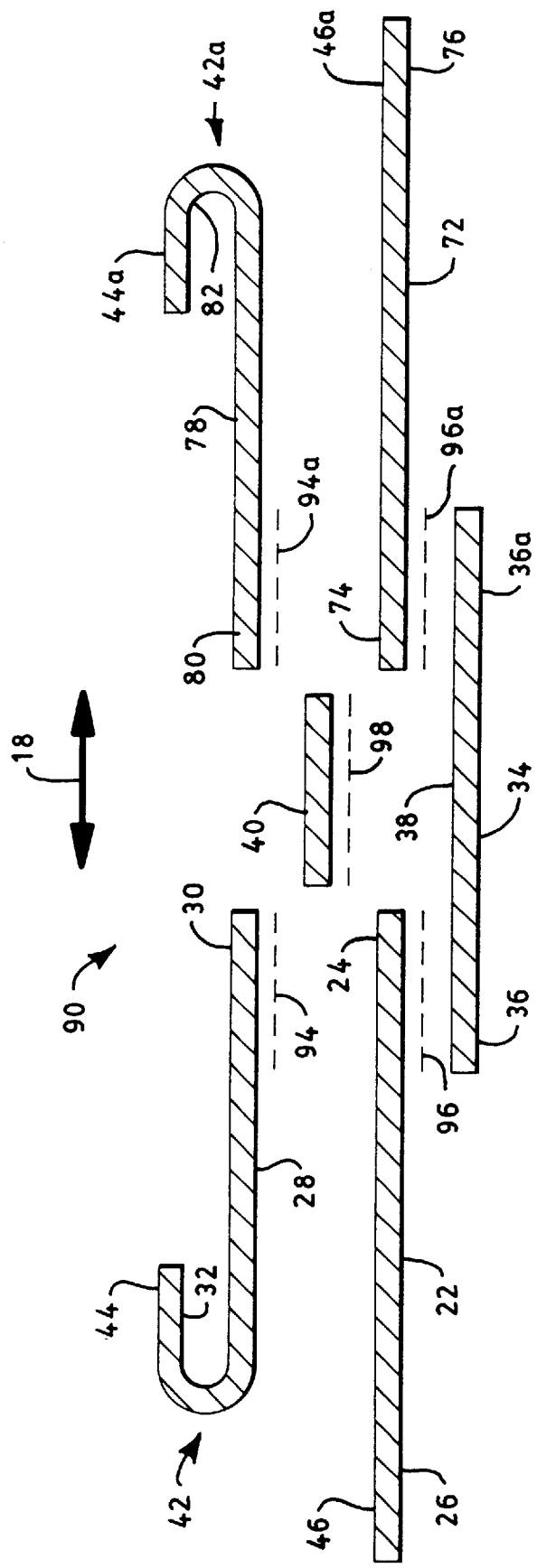
FIG. 7A representatively shows a schematic, expanded, cross-sectional, end view of the web assembly illustrated in FIG. 7 after marginal side portions of selected panel layers have been folded.
Figure 11:
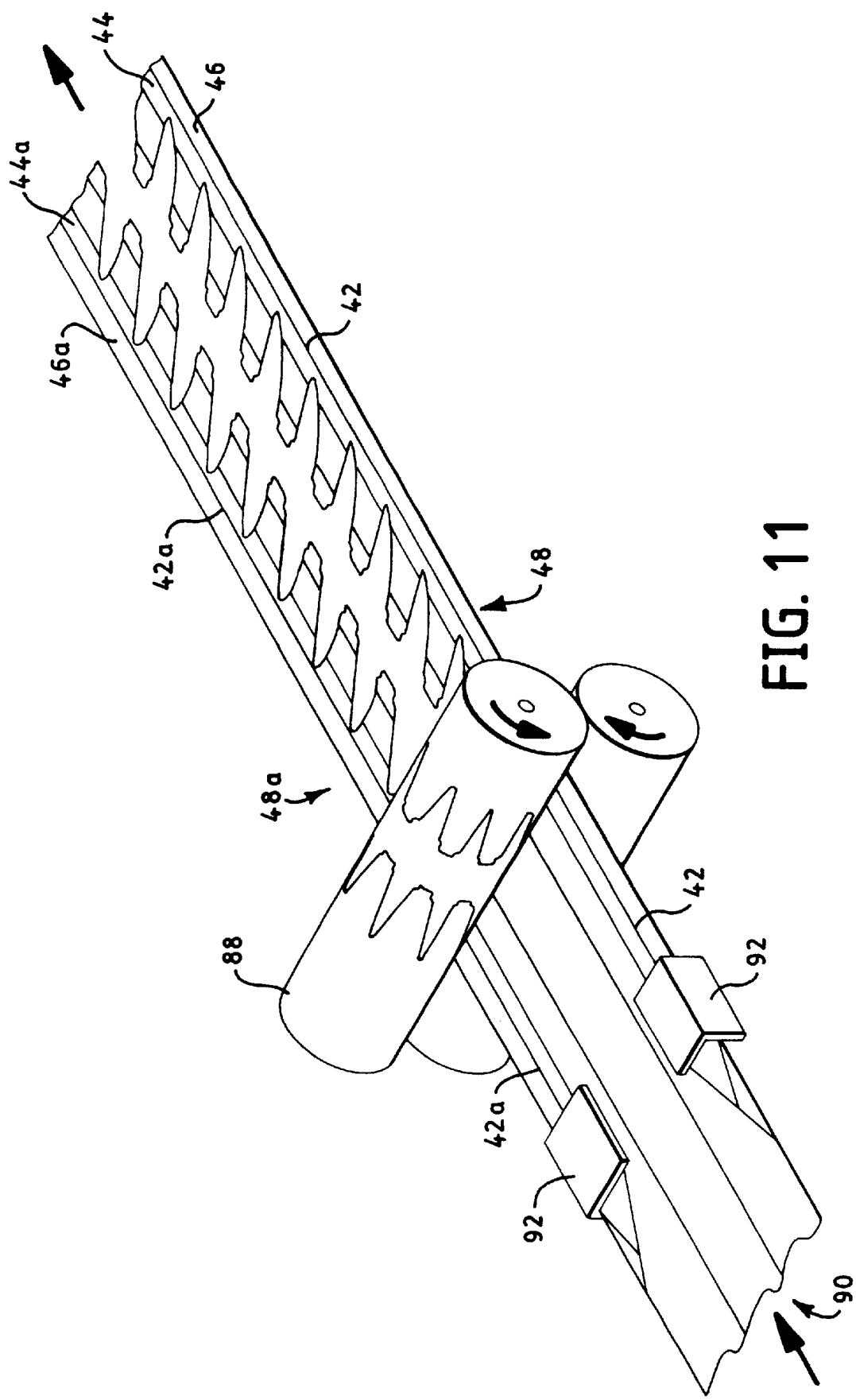
FIG. 11 shows a schematic, perspective view of a representative system for folding each individual assembly web before the dividing and shaping of the composite web to provide a set of the assembly webs.

The outboard portion 26, 32 of at least one of the first and second panel layers 22, 28 is folded to thereby provide a folded layer region 44 and a protruding layer region 46 (e.g. FIG. 3A). As representatively shown, the at least one panel layer can be operatively folded along a longitudinally extending fold line 42 which extends along the machine-direction 16 of the process and apparatus. A conventional folding mechanism, such as a folding board, a folding ski, a folding plow, a vacuum-assisted folder, an air-blast assisted folder or the like, can be employed to generate the desired fold. In the representatively shown configuration, a conventional folding board 92 (e.g. FIGS. 9 and 11) can be employed to fold the at least one panel layer along the selected folding line 42 to provide the folded layer 44.

In desired aspects, the first assembly web 48 is operatively severed to provide a plurality of individually panel assemblies 50. Each panel assembly 50 can be configured to include a tab web portion 52, a folded layer portion 54, and a protruding layer portion 56. For example, a conventional dividing or severing device, such as a rotary knife, a die cutter, a water cutter, a laser or other energy beam cutter, a high-energy particle-beam cutter or the like, may be employed to generate the desired panel assemblies. In the representatively shown configuration, a velocity-matched, pinch-cut mechanism can be employed to separate the assembly web 48 into the plurality of individual web assemblies 50.

The process and apparatus of the invention can further include the providing of the third panel layer 72 having its third inboard portion 74 and its third outboard portion 76. The fourth panel layer 78 is positioned onto the third panel layer 72, and the fourth panel layer 78 has its fourth inboard portion 74 and its fourth outboard portion 76. The inboard portion 74 of the third panel layer 72 is attached to the inboard portion 80 of the fourth panel layer 78. Additionally, a second side region 36a of the tab web 34 is attached to the inboard portion of at least one of the third and fourth panel layers 72, 78 to provide a composite web 90. The various constructions and assemblies with respect to the third panel layer, the fourth panel layer and the tab web 34 can be similar to those described and employed with respect to the first panel layer, the second panel layer and the tab web.

Figure 8:
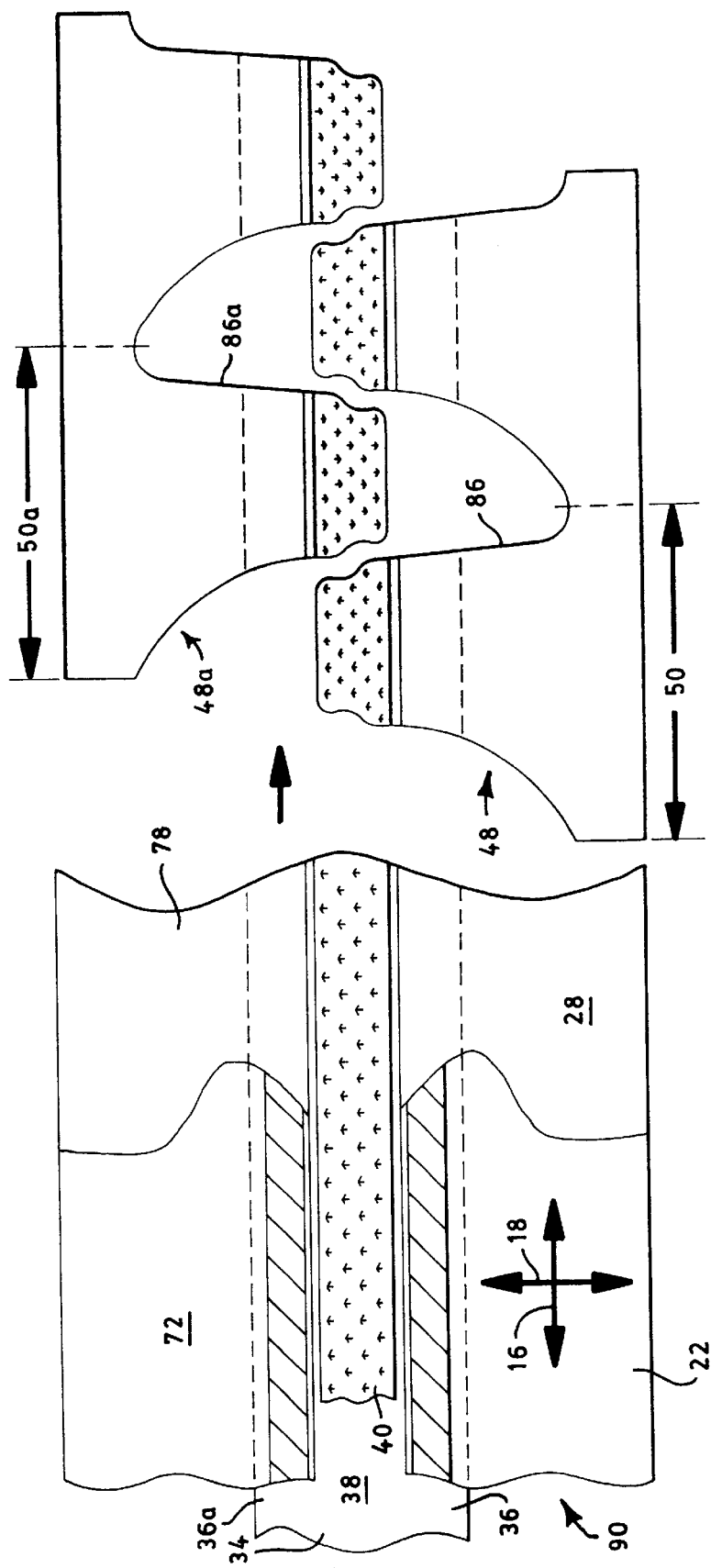
FIG. 8 representatively shows a top view of a sequence wherein the composite web (in a partially cut-away view) has been folded along desired, longitudinally extending fold lines before the shaping and dividing of the composite web to form a set of assembly webs.
Figure 8A:
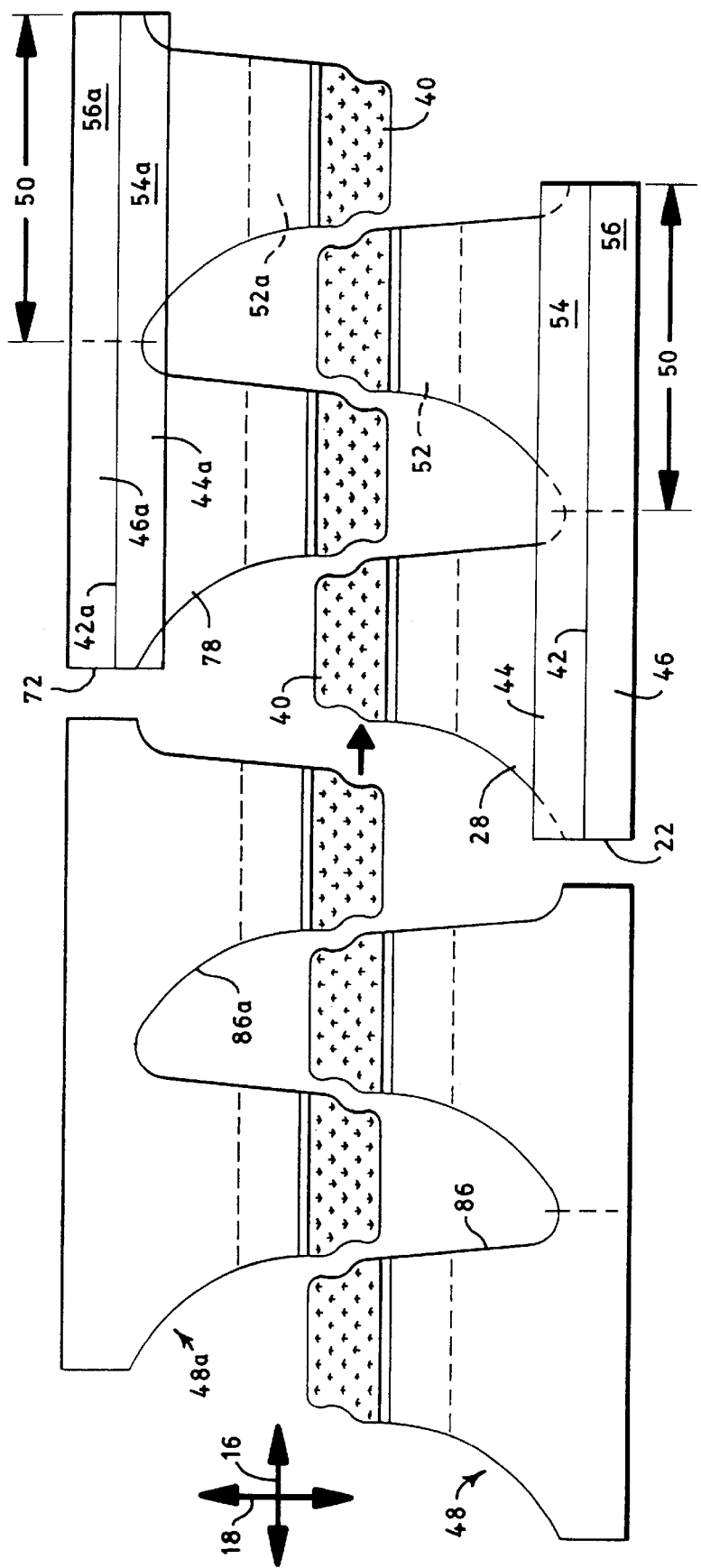
FIG. 8A representatively shows a schematic, top view of a sequence wherein a separated set of shaped assembly webs (in a partially cut-away view) have been folded along a longitudinally extending fold line after the shaping of the individual assembly webs.

As representatively shown in FIGS. 8, 8A and 9, the process and apparatus can include a dividing of at least the tab web 34 along at least one generally longitudinally extending serpentine line 86 to provide the first assembly web 48 and at least a second assembly web 48a. In the various configurations of the invention, any conventional severing mechanism can be employed to form the desired serpentine division line or lines. The shown arrangement can, for example, employ a conventional die cutting system 88 (e.g. FIGS. 9 and 11).

The second assembly web 48a can also be severed to provide a second plurality of individual, complementary panel assemblies 50a. The severing of the second assembly web can be conducted in a manner that is similar to that employed with the first assembly web 50. Also, the outboard portion of at least one of the third and fourth panel layers 72, 78 can similarly be folded along a longitudinally extending, complementary fold line 42a to thereby provide a complementary folded layer 44a and a complementary protruding layer 46a. Each complementary panel assembly 50a can be configured to include a complementary tab web portion 52a, a complementary folded layer portion 54a and a complementary protruding layer portion 56a. The complementary protruding layer portion 56a of at least one complementary panel assembly 50a can be attached to an opposed side section 68a of the first waistband portion 62 of the article segment 60. Additionally, the complementary folded layer portion 54a of the at least one complementary panel assembly 50a can be attached to its appointed side section 70a of the second waistband portion 64 of the article segment.

A particular aspect of the invention can include a dividing of at least the tab web 34 along the first serpentine line 86, and along a generally longitudinally extending second serpentine line 86a to thereby provide a undulating, serpentine strip section (not shown) between the first and second serpentine lines. The strip section can be removed to provide the first assembly web 48 and the second assembly web 48a.

In another aspect, the first panel layer 22, the second panel layer 28 and the tab web 34 can be divided along the generally longitudinally extending first serpentine line 86, and the third panel layer 72, the fourth panel layer 78 and the tab web 34 can be divided along the generally longitudinally extending second serpentine line 86a to thereby provide the undulating strip section between the first and second serpentine lines. The strip section can then be removed to provide the first assembly web 48 and a second assembly web 48a.

The serpentine division lines 86 and 86a extend generally longitudinally along the machine-direction 16. As representatively shown, each of the division lines can divide the tab web 34 and can have portions which extend to divide the first and second panel layers, or the third and fourth panel layers. The serpentine division lines 86 and 86a are desirably non-intersecting, and each of the serpentine lines can have longitudinally extending portions and generally laterally extending portions. In addition, each of the serpentine division lines can repeatedly traverse across a complete lateral width of the fastening mechanism 40, and can extend generally longitudinally along a medial region of the composite web 90 to provide for the serpentine strip section. The alternately traversing, side-to-side sections of each serpentine division line can optionally include retroceding portions thereof to provide for distinctively shaped fastening tabs.

The cooperating division lines 86 and 86a can operatively generate a substantially continuous, serpentine strip having substantially regularly repeating, periodic edge contours. The serpentine strip can then be readily removed away from the composite web 90 by employing a conventional transporting system, such as a system including a guide roller and/or a conventional vacuum duct system. Examples of suitable techniques for generating and processing the serpentine strip are described in U.S. Pat. No. 5,759,317 entitled PROCESS FOR MAKING A MECHANICAL FASTENER by D. A. Justmann which was issued Jun. 2, 1998 (attorney docket No. 12,637), the entire disclosure of which is incorporated herein by reference in a manner that is consistent herewith.

In a desired aspect, the folding of the outboard portion of the at least one of the first and second panel layers 22, 28 can occur before the dividing along the first serpentine line 86. Additionally, the folding of the outboard portion of the at least one of the third and fourth panel layers 72, 78 can occur before the dividing along the second serpentine line 86a.

Figure 13:
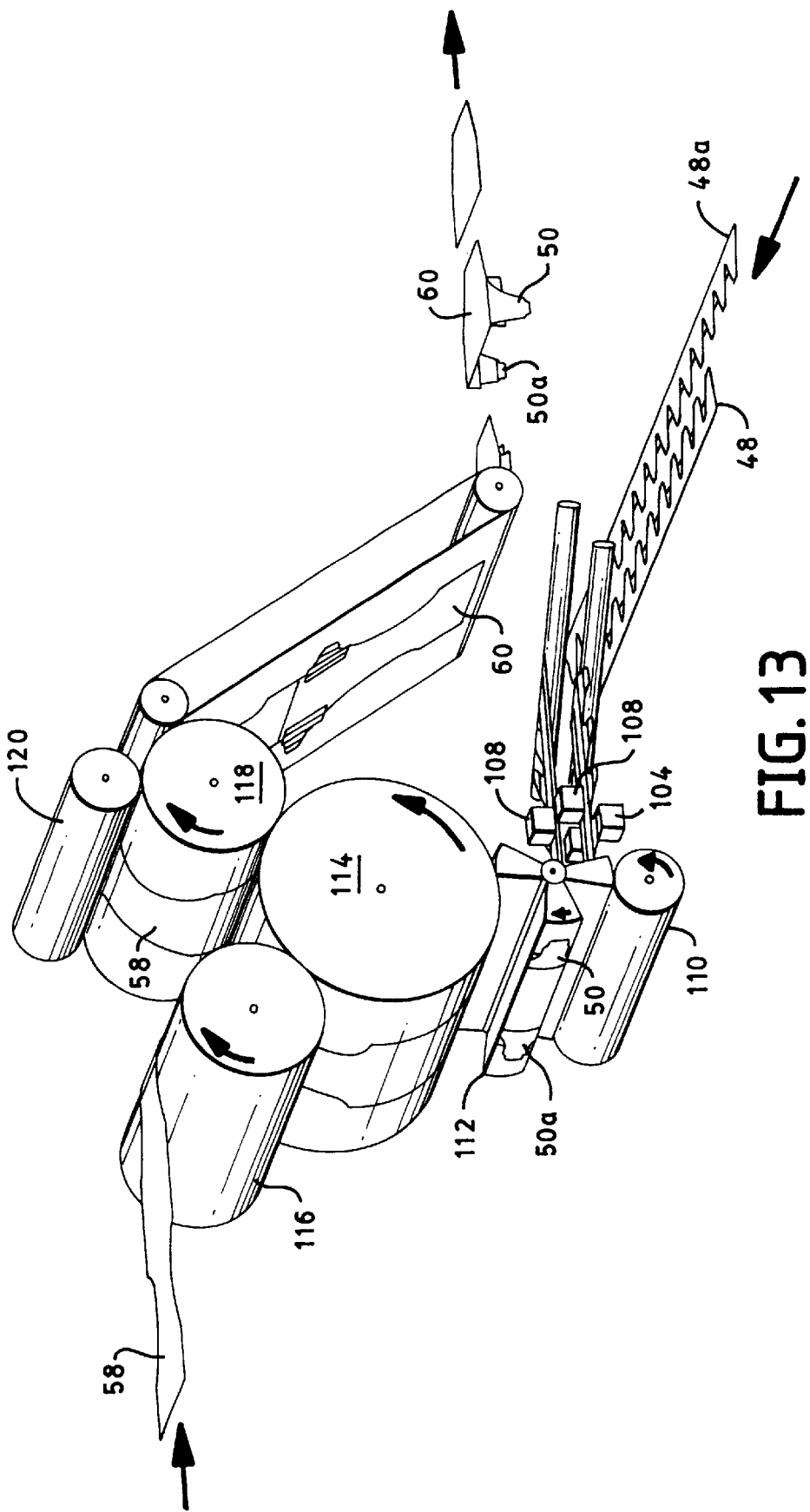
FIG. 13 of another representative system for forming individual fastener/panel assemblies, and applying and assembling the individual panel assemblies to an article web to provide a series of final articles, wherein the system employs an alternative arrangement of adhesive applicators.
Figure 14B:
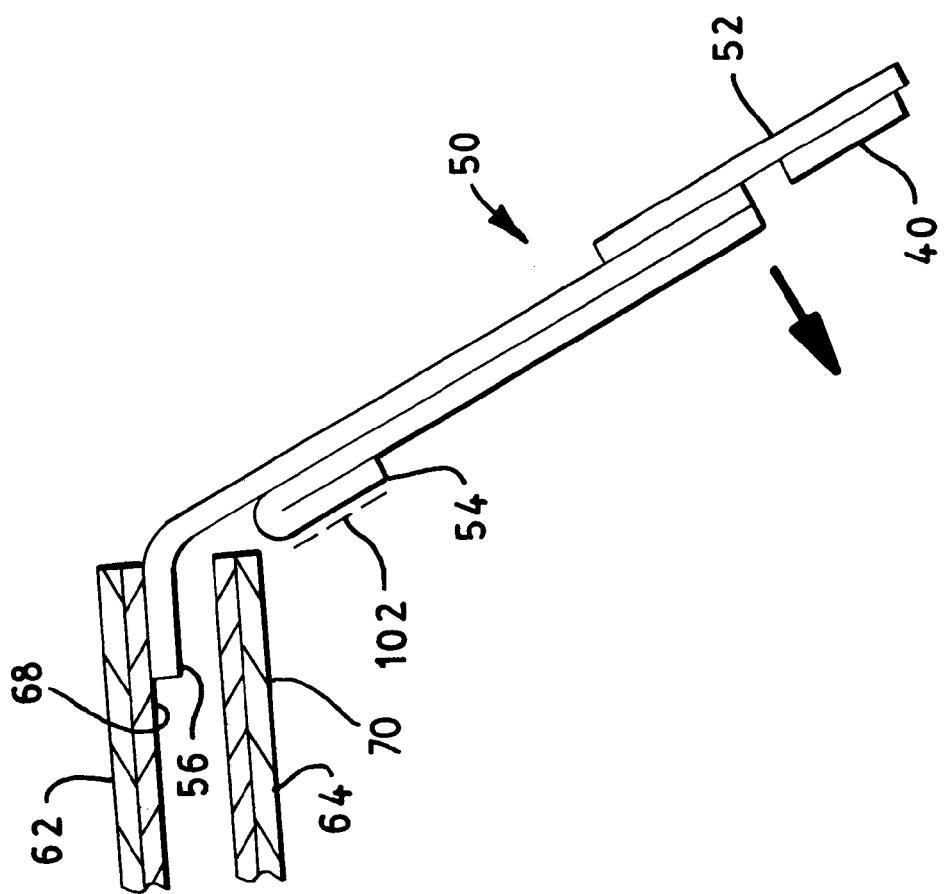
FIG. 14B representatively shows a schematic, expanded, edgewise view of a panel assembly being turned around a terminal edge of the second waistband portion of the article segment.
Figure 14C:
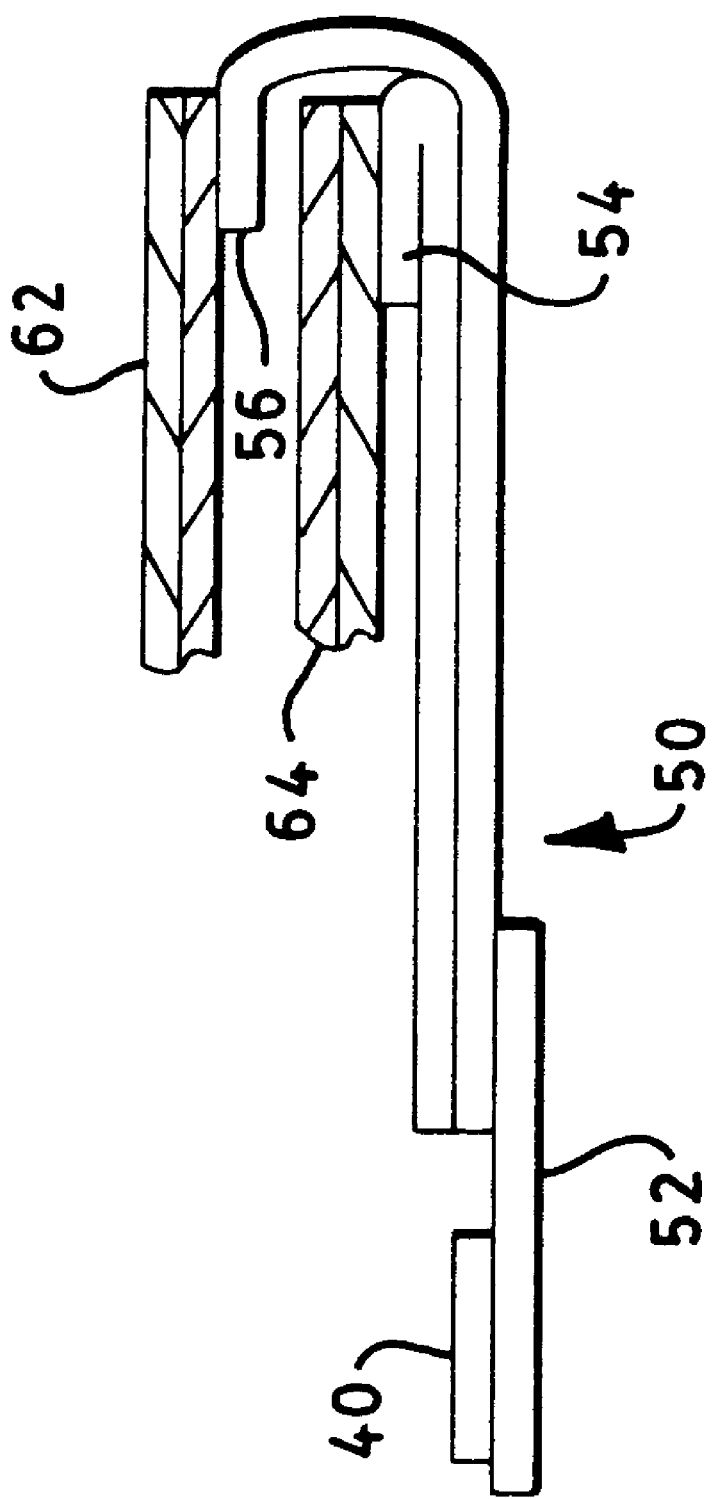
FIG. 14C representatively shows a schematic, expanded, edgewise view of a panel assembly after the folded portion of the panel assembly has been operatively joined and assembled to the second waistband portion of the article segment.

In another aspect, the folding of the outboard portion of the at least one of the first and second panel layers 22, 28 can occur after the dividing along the first serpentine line 86. Additionally the folding of the outboard portion of the at least of the third and fourth panel layers 72, 78 can occur after the dividing along the second serpentine line 86a. An operative first attaching mechanism 100 can be incorporated to secure the protruding layer portions 56, 56a of the individual panel assemblies 50, 50a at their appointed locations on their corresponding article segments. Any operative attaching mechanism may be employed. In particular arrangements, the attaching mechanism may be an adhesive bond, an ultrasonic bond, or the like, as well as combinations thereof. As representatively shown in FIGS. 12 and 13, for example, a first adhesive applicator system 104 can be configured to operatively apply a selected pattern of a first adhesive onto an appointed securement surface of the protruding layers 46 and/or 46a to provide a selected arrangement of the first attaching mechanism 100. In desired arrangements, the first adhesive can be configured to provide a substantially permanent bond between the protruding layer portions 56, 56*a* of the individual panel assemblies and their corresponding, attached regions of article web segments 60. As representatively shown in the arrangement illustrated in FIG. 13, the applicator system 104 can desirably be located relatively close to the cutter 110 to reduce the contacting of applied adhesive against any processing equipment that may be positioned between the applicator system 104 and the cutter 110.

In addition, a second attaching mechanism 102 is incorporated to secure the folded layer portions 54, 54*a* of the individual panel assemblies 50, 50*a* at their appointed locations on their corresponding article segments. Any operative attaching mechanism may be employed. In particular arrangements, the second attaching mechanism may be an adhesive bond, a hook-and-loop attachment, another interengaging mechanical attachment, or the like, as well as combinations thereof. As representatively shown, a selected pattern of a second adhesive applicator 108 can be configured to apply a second adhesive onto an appointed securement surface 109 of the folded layers 44 and/or 44*a* to provide a selected arrangement of the second attaching mechanism 102. In desired arrangements, the second adhesive can be configured to provide a relatively lower strength passive bond between the folded layer portions 54, 54*a* of the individual panel assemblies and their corresponding attached regions of their appointed article segments 60.

The first assembly web 48 and/or the second assembly web 48*a* can be severed by employing any conventional separating device, such as the representatively shown cut-off knife 110. Alternatively, other separating devices, such as those described elsewhere in the present disclosure, may be employed.

To provide the desired article segments 60, a selected article web 58 can be delivered into the process and apparatus by employing any conventional transporting system. The article web 58 can typically include an interconnected plurality of individual article segments 60, and each article segment 60 is desirably provided with the article segment having a first waistband portion 62, a second waistband portion 64, and an intermediate portion 66 that interconnects the first and second waistband portions.

The transporting system may, for example, include a spreader roll 118 which directs the article web 58 onto an assembly drum 114. The article web is typically directed around the assembly drum 114 at a selected machine-speed. The machine-speed of the article web, however, maybe greater than or less than the speed of the assembly webs 48 and 48*a* being delivered into the cut-off knife 110. To compensate for the differences in speed, a matched-speed applicator 112 can be employed to move the individual panel assemblies 50 away from the position of the cut-off knife 110 and transfer the individual panel assemblies 50 onto their appointed positions along the moving article web 58.

Various matched-speed applicators may be employed. For example, the matched-speed applicator may include a vacuum slip roll, a segmented roll having sections that move separately from one another, a system of arms rotating about a common axis, or the like, as well as combinations thereof. Accordingly, the matched-speed applicator can include any conventional apparatus and method for receiving discrete parts traveling at one speed and applying the parts to a web traveling at a different speed. In desired arrangements, the devices can, for example, receive discrete elongated elastic components separated from a continuously moving web of elongated elastic material traveling at a certain speed, and apply the discrete elongated elastic components onto a product web of interconnected articles traveling at a different speed. Examples of such devices are disclosed in U.S. Pat. No. 5,716,478 entitled APPARATUS AND METHOD FOR APPLYING DISCRETE PARTS ONTO A MOVING WEB by J. L. Boothe et al. which was issued Feb. 10, 1998 (attorney docket No. 12,243). Other examples are described in U.S. Pat. No. 6,022,443 entitled METHOD AND APPARATUS FOR PLACING DISCRETE PARTS ONTO A MOVING WEB by G. J. Rajala et al. which was issued Feb. 8, 2000 (attorney docket No. 10,581); and in U.S. Pat. No. 6,149,755 entitled MACHINE AND PROCESS FOR PLACING DISCRETE COMPONENTS ON A MOVING WEB WITH VELOCITY MATCHED PLACEMENT AND INTEGRAL BONDING by P. S. McNichols et al, which was issued Nov. 21, 2000 (attorney docket No. 13,010) The entire disclosures of these documents are incorporated herein by reference in a manner that is consistent herewith.

After the individual panel assemblies 50 have been operatively attached to their appointed positions on the individual article segments 60 of the article web 58, the article web can be directed onto the representatively shown transfer anvil roll 118. A separating device such as the representatively shown final cut-off knife 120, can divide the article web 58 and separate the individual article segments 60 from the article web 58. Alternatively, any conventional severing device may be employed to provide the desired separating and segmenting operation.

The individual article segments 60 can then be directed to a conventional article-folding device, such as the representatively shown half-folder 122. The transverse folding of each article segment 60 can be configured to operatively place its first waistband portion 62 in a facing relation with and substantially adjacent to its corresponding, second waistband portion 64. The folding of the individual article segment 60 can also place the second waistband portion 64 operatively adjacent the panel assemblies 50, 50*a* that have been attached to the corresponding first waistband portion 62 of that article segment. More particularly, the side sections 70 of the second waistband portion 64 can be operatively positioned substantially subjacent or substantially superjacent to the folded layer portion 54 of the individual panel assembly 50, as desired. The transversely extending fold line of each article segment extends through the intermediate portion 66 of the article segment. In desired arrangements, the transverse folding of each article segment 60 can fold that article segment substantially in half.

A conventional folding mechanism (not shown), such as a folding board, a folding ski, a folding plow, a vacuum-assisted folder, an air-blast assisted folder, or the like, can then be employed to turn the folded layer portion 54 of the individual panel assembly 50 around the corresponding side sections of the adjacently positioned first and second waistband portions to attach the folded layer portion 54 onto its appointed region of the side section of the second waistband portion 64 of the article segment 60. Additionally, the selected folding mechanism can be employed to turn the tab web portion 52 of the individual panel assembly 50 around the side sections of the first and second waistband portions of its corresponding article segment 60. The turning of the folded layer portion 54 and/or the tab web portion 52 can traverse such portion through any arc that is required to operatively position that portion onto the desired location of the second waistband portion. In the representatively shown configuration, the desired turning operations can traverse the selected turned portion through an arc angle of about 180°.

After forming the desired securement bond between the folded layer portion 54 and the side section 70 of the second waistband portion 64, each article segment can be further processed. For example, each folded article segment can be directed into a system of compression nip rollers to enhance the attachments between the individual panel assemblies 50 and their corresponding article segments 60.

In the various configurations of the invention, the particular patterns of applied adhesive may be substantially continuous or discontinuous. During certain movements and transfers of the assembly webs 48 and 48a, one or more of the applied patterns of adhesive may have an arrangement or distribution which causes the adhesive to contact a process component, such as a roller or turn bar, for a limited time. To help prevent excessive adhesive build-up and/or sticking of the assembly web on the contacting surfaces of the processing components, the appropriate contact surfaces of the processing components can be coated with an easy-release, low-adhesion or substantially zero-adhesion material. Conventional easy-release coatings are well known in the art, and such coatings can, for example, include polytetrafluorouethylene or the like.

Having described the invention in rather full detail, it will be readily apparent that various changes and modifications can be made without departing from the spirit of the invention. All of such changes and modifications are contemplated as being within the scope of the invention as defined by the subjoined claims.

What is claimed is:

1. A process for forming an article, the process comprising:
    a providing of a first panel layer having a first inboard portion and a first outboard portion;
    a positioning of a second panel layer onto the first panel layer, the second panel layer having a second inboard portion and a second outboard portion;
    an attaching of the first inboard portion to the second inboard portion;
    an attaching of a side region of a tab web to the inboard portion of at least one of the first and second panel layers to provide a first assembly web;
    a providing of a fastening mechanism attached to an appointed securement surface of the tab web;
    a folding of the outboard portion of at least one of the first and second panel layers, thereby providing a folded layer and a protruding layer;
    a severing of the first assembly web to provide a plurality of individual panel assemblies;
    wherein each individual panel assembly includes a tab web portion, a folded layer portion and a protruding layer portion;
    a providing of an article segment having a first waistband portion, a second waistband portion and an intermediate portion that interconnects the first and second waistband portions;
    an attaching of the protruding layer portion of at least one individual panel assembly to a side section of the first waistband portion of the article segment;
    a transverse folding of the article segment along a transversely extending fold line to provide a folded article segment; and
    an attaching of the folded layer portion of the at least one individual panel assembly to a side section of the second waistband portion of the folded article segment.

2. The process as recited in claim 1, further including a turning of the folded layer portion of the at least one individual panel assembly around the side section of the second waistband portion of the folded article segment.

3. The process as recited in claim 2, further including a turning of the tab web portion of the at least one individual panel assembly around the side section of the second waistband portion of the folded article segment.

4. A process for forming an article, the process comprising:
    a providing of a first panel layer having a first inboard portion and a first outboard portion;
    a positioning of a second panel layer onto the first panel layer, the second panel layer having a second inboard portion and a second outboard portion;
    an attaching of the first inboard portion to the second inboard portion;
    a providing of a third panel layer having a third inboard portion and a third outboard portion;
    a positioning of a fourth panel layer onto the third panel layer, the fourth panel layer having a fourth inboard portion and a fourth outboard portion;
    an attaching of the third inboard portion to the fourth inboard portion;
    an attaching of a first side region of a tab web to the inboard portion of at least one of the first and second panel layers and an attaching of a second side region of the tab web to the inboard portion of at least one of the third and fourth panel layers thereby providing a composite assembly web;
    a providing of a fastening mechanism attached to an appointed securement surface of the tab web
    a dividing of at least the tab web along at least one, generally longitudinally extending serpentine line to provide a first assembly web and at least a second assembly web
    a severing of the first assembly web to provide a plurality of individual panel assemblies;
    a folding of the outboard portion of at least one of the first and second panel layers to thereby provide a folded layer and a protruding layer;
    wherein each individual panel assembly includes a tab web portion, a folded layer portion and a protruding layer portion;
    a severing of the second assembly web to provide a plurality of individual, complementary panel assemblies;
    a folding of the outboard portion of at least one of the third and fourth panel layers to thereby provide a complementary folded layer and a complementary protruding layer;
    wherein each individual, complementary panel assembly includes a complementary tab web portion, a complementary folded layer portion and a complementary protruding layer portion.

5. The process as recited in claim 4, further including
    providing an article segment having a first waistband portion, a second waistband portion and an intermediate portion that interconnects the first and second waistband portions;
    an attaching of the protruding layer portion of at least one individual panel assembly to a side section of the first waistband portion of the article segment;
    an attaching of the complementary protruding layer portion of at least one complementary panel assembly to an opposed side section of the first waistband portion of the article segment.

6. The process as recited in claim 5, further including a transverse folding of the article segment along at least one transversely extending fold line to provide a folded article segment;

an attaching of the folded layer portion of the at least one individual panel assembly to a side section of the second waistband portion of the folded article segment; and an attaching of the complementary folded layer portion of the at least one complementary panel assembly to an opposed side section of the second waistband portion of the folded article segment.

7. The process as recited in claim 4, further including a dividing of the first panel layer, the second panel layer and the tab web along a generally longitudinally extending first serpentine line;

a dividing of the third panel layer, the fourth panel layer and the tab web along a generally longitudinally extending second serpentine line to thereby provide a strip section between the first and second serpentine lines; and a removing of the strip section to provide a first assembly web and at least a second assembly web.

8. The process as recited in claim 7, further including providing an article segment having a first waistband portion, a second waistband portion and an intermediate portion that interconnects the first and second waistband portions;

an attaching of the protruding layer portion of at least one individual panel assembly to a side section of the first waistband portion of the article segment;

an attaching of the complementary protruding layer portion of at least one complementary panel assembly to an opposed side section of the first waistband portion of the article segment.

9. The process as recited in claim 8, further including a transverse folding of the article segment along at least one transversely extending fold line to provide a folded article segment;

an attaching of the folded layer portion of the at least one individual panel assembly to a side section of the second waistband portion of the folded article segment; and an attaching of the complementary folded layer portion of the at least one complementary panel assembly to an opposed side section of the second waistband portion of the folded article segment.

10. The process as recited in claim 9, wherein the folding of the outboard portion of at least one of the first and second panel layers occurs before dividing along the first serpentine line.

11. The process a recited in claim 9, wherein the folding of the outboard portion of at least one of the first and second panel layers occurs after dividing along the first serpentine line.

12. The process as recited in claim 9, wherein the folding of the outboard portion of at least one of the third and fourth panel layers occurs before dividing along the second serpentine line.

13. The process as recited in claim 9, wherein the folding of the outboard portion of at least one of the third and fourth panel layers occurs after dividing along the second serpentine line.

* * * * *